United States Patent
Susaki et al.

(10) Patent No.: US 7,041,818 B2
(45) Date of Patent: May 9, 2006

(54) DDS COMPOUND AND METHOD FOR MEASUREMENT THEREOF

(75) Inventors: Hiroshi Susaki, Tokyo (JP); Kazuhiro Inoue, Tokyo (JP); Hiroshi Kuga, Tokyo (JP); Masahiro Ikeda, Tokyo (JP); Yoshinobu Shiose, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 131 days.

(21) Appl. No.: 10/822,661

(22) Filed: Apr. 13, 2004

(65) Prior Publication Data

US 2004/0192644 A1 Sep. 30, 2004

Related U.S. Application Data

(63) Continuation of application No. 09/807,980, filed as application No. PCT/JP99/06016 on Oct. 29, 1999, now Pat. No. 6,811,996.

(30) Foreign Application Priority Data

Oct. 30, 1998 (JP) .................................. 10/310130
Nov. 19, 1998 (JP) .................................. 10/329272

(51) Int. Cl.
*A61K 31/47* (2006.01)
*A61K 47/26* (2006.01)
*A61K 47/30* (2006.01)
*A61K 47/48* (2006.01)

(52) U.S. Cl. ........................................ 536/112; 514/59

(58) Field of Classification Search ..................... None
See application file for complete search history.

(56) References Cited

U.S. PATENT DOCUMENTS

| | | | |
|---|---|---|---|
| 4,386,026 A | 5/1983 | Ponpipom et al. | ............ 536/53 |
| 5,658,592 A | 8/1997 | Tanihara et al. | ............ 424/488 |
| 5,688,931 A | 11/1997 | Nogusa et al. | ................ 536/20 |
| 5,738,864 A | 4/1998 | Schacht et al. | ............ 424/426 |
| 5,814,656 A | 9/1998 | Saavendra et al. | .......... 514/426 |
| 5,846,974 A | 12/1998 | Kallman et al. | ............ 514/269 |
| 5,886,143 A | 3/1999 | Theodore et al. | ............ 530/322 |
| 6,338,843 B1 | 1/2002 | Duncan et al. | .......... 424/78.18 |
| 6,340,461 B1 | 1/2002 | Terman | .................... 424/193.1 |
| 6,368,598 B1 | 4/2002 | D'Amico et al. | ........ 424/181.1 |
| 6,436,912 B1 | 8/2002 | Inoue et al. | .................. 514/59 |
| 6,811,996 B1 * | 11/2004 | Inoue et al. | .................. 435/24 |
| 2003/0171262 A1 | 9/2003 | Inoue et al. | .................. 514/8 |

FOREIGN PATENT DOCUMENTS

| | | |
|---|---|---|
| EP | 624377 | 11/1994 |
| EP | 0640622 | 3/1995 |

(Continued)

OTHER PUBLICATIONS

English Language Abstract of JP 5-178986, (Jul. 20, 1993).

(Continued)

*Primary Examiner*—Jeffrey Edwin Russel
(74) *Attorney, Agent, or Firm*—Greenblum & Bernstein, P.L.C.

(57) ABSTRACT

A DDS compound comprising a carboxy($C_{1-4}$)alkyldextran polyalcohol modified with a saccharide compound and a residue of drug compound bound to the carboxy($C_{1-4}$) alkyldextran polyalcohol, and a method for measuring a DDS compound in which a polymer carrier and a residue of drug compound are bound to each other by means of a spacer comprising 2 to 8 amino acids linked by peptide bond(s), which comprises the steps of treating the DDS compound with a peptidase, and measuring the resulting hydrolysate.

20 Claims, 6 Drawing Sheets

Accumulation of DDS compound in liver

FOREIGN PATENT DOCUMENTS

| | | |
|---|---|---|
| EP | 0712635 | 5/1996 |
| EP | 0916348 | 5/1999 |
| JP | 5-178986 | 7/1993 |
| JP | 5-202085 | 8/1993 |
| JP | 5-222187 | 8/1993 |
| JP | 6-87746 | 3/1994 |
| JP | 7-70311 | 3/1995 |
| JP | 7-228688 | 8/1995 |
| JP | 7-84481 B2 | 9/1995 |
| JP | 8-85703 | 4/1996 |
| JP | 8-319317 | 12/1996 |
| JP | 9-118699 | 5/1997 |
| JP | 2774429 B2 | 7/1998 |
| JP | 2774417 B2 | 9/1998 |
| WO | 94/19376 | 9/1994 |
| WO | 97/46260 | 12/1997 |
| WO | 98/19705 | 5/1998 |
| WO | 98/56424 | 12/1998 |
| WO | 99/61061 | 12/1999 |

OTHER PUBLICATIONS

English Language Abstract of JP 5-222187, (Aug. 31, 1993).
English Language Abstract of JP 6-87746, (Mar. 29, 1994).
English Language Abstract of JP 7-70311, (Mar. 14, 1995).
English Language Abstract of JP 7-228688, (Aug. 29, 1995).
Cover Sheet of WO 92/14759, (Sep. 3, 1992).
English Language Abstract of JP 8-85703, (Apr. 2, 1996).
English Language Abstract of JP 9-118699, (May 6, 1997).
English Language Abstract of JP 8-319317, (Dec. 3, 1996).
English Language Abstract of JP 2774417, (Jul. 9, 1998).
English Language Abstract of JP 5-202085, (Aug. 10, 1993).
English Language Abstract of JP 2774429, (Jul. 9, 1998).
Abstracts of 10th Meeting of the Japan Society of Drug Delivery System, pp. 279 (1994).
Abstracts of 9th Annual Meeting of Japanese Society for the Study of Xenobiotics, Metabol. And Dispo. vol. 9, Supplement, pp. S27, S27, S292 (1994).
Abstracts of 19th Seminar of Trends in Research and Development, pp. D-9 to D12, (1995).
Abstracts of 12th Colloid and Interface Technology Symposium, The Chemical Society of Japan, pp. 51-58 (1995).
Naokazu Murahashi et al., "Hepatic Accumulation of Glutamic Acid Branched Neogalactosyllipid Modified Liposomes", Biol. Pharm. Bull., vol. 20, No. 3, pp. 259-264 (1997).
Tamio Sugawara et al., "Synthesis of 8-Aminooctyl glycopyranosides and of their Conjugates with Poly(L-Glutamic Acid) having a 2-(4-hydroxyphenyl)ethylamino Group for Radiolabeling", Carbohydrate Research, vol. 238, pp. 163-184 (1993).
Hideki Hirabayashi et al., "Development and Pharmacokinetics of Galactosylated Poly-L-Glutamic Acid as a Biodegradable Carrier for Liver-Specific Drug Delivery", Pharmaceutical Research, vol. 13, No. 6, pp. 880-884 (1996).
Akinori Gonsho et al., "Tissue-Targeting Ability of Saccharide-Poly(L-Lysine) Conjugates", Biol. Pharm. Bull., vol. 17, No. 2, pp. 275-282 (1994).
Makiya Nishikawa et al., "Synthesis and Pharmacokinetics of a New Liver-Specific Carrier, Glycosylated Corboxymethyl-Dextran, and Its Application to Drug Targeting", Pharmaceutical Research, vol. 10, No. 9, pp. 1253-1261 (1993).
Ruth Duncan et al., "Fate of N-(2-Hydroxyproply) Methacrylamide Copolymers with Pendent Galactosamine Residues After Intravenous Administration to Rats", Biochimica et Biophysica Acta, vol. 880, pp. 62-71 (1986).
Shuji Kojima et al., "Tissue Distribution of Radioiodinated Neoglycoproteins and Mammalian Lectins", Biol. Chem. Hoppe-Seyler, vol. 371, pp. 331-338 (1990).
Grietje Molema et al., "Neoglycoproteins as Carriers for Antiviral Drugs: Synthesis and Analysis of Protein-Drug conjugates", J. Med. Chem., vol. 34, pp. 1137-1141 (1991).
Kurisawa et al., J. Biomater Sci Polym Ed. 1997; 8(9):691-708.
Hashida et al. Targeted delivery of drugs and proteins to the liver via receptor-mediated endocytosis. Journal of Controlled Release. 1997, vol. 46, p. 129-137.
Kichler et al. Versatile synthesis of bi-and tri-antennary galacctose ligands . . . Glycoconjugate Journal. 1995, vol. 12, pp. 275-281.
Li et al. Synthesis, Metal Chelate Stability Studies . . . Bioconjugate Chemistry. vol. 4, No. 4, pp. 275-283 (1993).
Sharma et al. Treatment of Lymphoid Cell Malignancy with in-114m Labelled Autologous Lymphocytes. Anticancer Research. vol. 17, pp. 1815-1822(1997).
M. Nishikawa et al., Pharmaceutical Research, vol. 10, No. 9, pp. 1253-1261, (1993).
J. Murata et al., Journal of Biomaterials Science Polymer Edition, vol. 8, No. 12, pp. 931-946 (1997).
R. Duncan et al., "Preclinical evaluation of polymer-bound doxorubicin", Journal of Controlled Release, vol. 19, pp. 331 to 345 (1992).

* cited by examiner

Accumulation of DDS compound in liver

DDS COMPOUND AND METHOD FOR MEASUREMENT THEREOF

CROSS-REFERENCE TO RELATED APPLICATIONS

This application is a continuation of application Ser. No. 09/807,980, filed Jul. 2, 2001, now U.S. Pat. No. 6,811,996, which is a National Stage Application of International Application No. PCT/JP99/06016, filed Oct. 29, 1999, which was not published in English under PCT Article 21(2), and which claim priority of Japanese Application Nos. 10-310130, filed Oct. 30, 1998, and 10-329272, filed Nov. 19, 1998. The entire disclosure of application Ser. No. 09/807,980 is considered as being part of the disclosure of this application, and the entire disclosure of application Ser. No. 09/807,980 is expressly incorporated by reference herein in its entirety.

TECHNICAL FIELD

The present invention relates to a DDS compound (DDS: drug delivery system) in which a carboxy($C_{1-4}$)alkyldextran polyalcohol modified with a saccharide compound and a drug compound such as antineoplastic agents are bound to each other. The present invention also relates to a method for measurement of a DDS compound in which a polymer carrier and a drug compound such as antineoplastic agents are bound to each other.

BACKGROUND ART

Antineoplastic agents, used for treatment of solid cancers such as lung cancer or digestive organ carcinomas and blood cancers such as leukemia, are systemically administered through routes of administration such as intravenous or oral administration, and then, are distributed to certain tumorous sites and inhibit or suppress the proliferation of cancer cells to exhibit their therapeutic efficacy. However, the systemically-administered antineoplastic agents are rapidly taken into livers and reticuloendothelial organs from blood, or rapidly excreted into urine, and accordingly, their blood concentrations may be sometimes too low to distribute to tumorous sites sufficiently. In addition, common antineoplastic agents themselves do not distribute tumorous sites selectively (tumor selectivity), and therefore, the antineoplastic agents are uniformly distributed over various tissues and cells of the whole body and act as cytotoxins also against normal cells and tissues, which results in problems of the appearance of adverse effects, e.g., emesis, pyrexia, or alopecia at an extremely high rate. Therefore, it has been desired to develop a means of efficiently and selectively distributing antineoplastic agents to tumorous sites.

As one of such means, a process was proposed in which a polysaccharide derivative having carboxyl groups is used as a polymer carrier, and an antineoplastic agent is bound to the polymer carrier to delay the disappearance of the antineoplastic agent from blood and to enhance selectivity to tumor tissues. For example, International Publication WO94/19376 discloses a DDS compound in which a peptide chain (the number of amino acid residues: 1 to 8) is bound to a carboxyl group of a polysaccharide having carboxyl groups, and doxorubicin, daunorubicin, mitomycin C, bleomycin or the like is further bound by means of the peptide chain. In addition, Japanese Patent Publication (KOKOKU) No. (Hei) 7-84481/1995 discloses a DDS compound in which the aforementioned antineoplastic agent is introduced into a carboxymethylated mannoglucan derivative by means of a Schiff base or an acid amide bond.

These DDS compounds (also referred to as "drug complexes") are characterized in that they have more excellent antineoplastic activity, reduced toxicity and adverse effects compared to antineoplastic agents, per se, that are bound to polymer carriers. The inventors of the present invention have provided a DDS compound which is formed by binding a polymer carrier such as polysaccharide compounds to a drug compound such as antineoplastic agents by means of a spacer consisting of one to eight amino acids, and which can site-selectively distribute the drug compound such as antineoplastic agents to target tissues (International Publication WO97/46260). They have also found that a carboxy($C_{1-4}$) alkyldextran polyalcohol has highly desirable characteristics as a polymer carrier, and provided a DDS compound containing a carboxy($C_{1-4}$)alkyldextran polyalcohol as a polymer carrier (the above mentioned International Publication).

As for technologies relating to DDS compounds utilizing polyalcoholized polysaccharide derivatives as polymer carriers, some reports are available, for example, "Researches on polysaccharide-peptide-doxorubicin complexes—Correlations between stabilities of polysaccharide carriers in blood and their anti-neoplastic activities" (Abstracts of 10th Meeting of the Japan Society of Drug Delivery System, 279, 1994); "Researches on polysaccharide-peptide-doxorubicin complexes—Pharmacokinetics and anti-neoplastic activity" (Abstracts of 9th Annual Meeting of Japanese Society for the study of xenobiotics, 292, 1994); Abstracts of 19th Seminar of Trends in Research and Development (held by The Organization for Pharmaceutical Safety and Research), D-9, 1995; and "Researches on drug delivery to a tumor tissue by polysaccharide carriers" (Abstracts of 12th Colloid and Interface Technology Symposium, The Chemical Society of Japan, 51, 1995).

As means for enhancing organ selectivity of polysaccharide compounds and the like, for example, saccharide-modified polyglutamic acid derivatives (Japanese Patent Unexamined Publication (KOKAI) (Hei) No. 5-178986/1993), saccharide-modified polylysine derivatives (Japanese Patent Un-examined Publication (KOKAI) (Hei) No. 5-222187/1993), D-galactopyranosylgluconic acid derivatives of a poly-ε-substituted-L-lysine (Japanese Patent Unexamined Publication (KOKAI) (Hei) No. 7-70311/1995), saccharide-modified poly-ω-substituted-L-glutamic acid derivatives (Japanese Patent Unexamined Publication (KOKAI) (Hei) No. 7-228688/1995), polysaccharide compounds bound to a saccharide compound by means of a linker (Japanese Patent Unexamined Publication (KOKAI) (Hei) No. 8-85703/1996), glucosyl-protein derivatives (Japanese Patent Un-examined Publication (KOKAI) (Hei) No. 9-118699/1997) and the like have been known. However, any techniques for enhancing organ selectivity of DDS compounds have not polymer carrier.

When a DDS compound is clinically used in which a polymer carrier and a residue of a drug compound are linked to each other by means of a spacer containing an oligopeptide, it is necessary to accurately measure a blood concentration of the DDS compound, per se, and also to accurately measure a content of the residue of the drug compound, such as antineoplastic agents introduced to the DDS compound, to determine an appropriate dosage or to test lot differences of products. The measurements of a blood concentration of a DDS compound and a content of residue of a drug compound in the DDS compound have conventionally been performed by measuring the DDS compound directly, per se, based on fluorescence of the drug compound or its UV absorption without cleaving the drug compound or the drug compound bound with a part of the spacer from the DDS compound. Furthermore, a method based on NMR analysis of a DDS compound, per se, and a method of measuring a decomposed product obtained by an acid treatment of a DDS compound have also been proposed.

However, those methods have problems in that a quantitative measurement of a decomposed product by an acid treatment cannot be performed when the drug compound is susceptible to an acid, and accuracy of the NMR analysis is insufficient. Moreover, UV absorption of a residue of a drug compound present in a DDS compound may cause a shift of maximum absorption wavelength or a change in molar extinction coefficient relative to the drug compound itself because of effects of a polymer carrier or a peptide spacer, and therefore, it is generally difficult to accurately measure a content of a residue of a drug compound introduced into a DDS compound. It is extremely difficult to quantitatively measure a DDS compound in tissues after administration to living bodies by the methods based on NMR analysis or UV absorption.

DESCRIPTION OF THE INVENTION

An object of the present invention is to provide a means for enhancing organ selectivity (e.g., selectivity to liver or the like) of DDS compounds containing a carboxy($C_{1-4}$)alkyldextran polyalcohol as a polymer carrier, and to provide a DDS compound having the aforementioned characteristics.

Another object of the present invention is to provide a polysaccharide compound useful as a raw material for the manufacture of DDS compounds having the aforementioned characteristics.

A still further object of the present invention is to provide a method for measuring a DDS compound in which a polymer carrier and a residue of a drug compound are bound to each other by means of a spacer that comprises an oligopeptide. More specifically, the object of the present invention is to provide a method for accurately measuring the DDS compound, per se, or a content of the residue of the drug compound such as antineoplastic agents introduced to the DDS compound. Further specifically, the object of the present invention is to provide a method for determining an acurate concentration of the DDS compound in blood or a tissue after administration, or a method for determining of a content of the residue of the drug compound introduced to the DDS compound accurately.

The inventors of the present invention earnestly conducted intensive studies to achieve the foregoing objects, and as a result, found that a DDS compound with extremely high organ selectivity was obtainable by using a carboxy ($C_{1-4}$)alkyldextran polyalcohol modified with a saccharide compound as a polymer carrier, and that a DDS compound containing the carboxy($C_{1-4}$)alkyldextran polyalcohol bound to galactose, in particular, had excellent liver selectivity.

Moreover, the inventors of the present invention also found that a blood concentration of a DDS compound or a content of residues of a drug compound introduced to the DDS compound can be accurately and easily determined by treating a DDS compound with a peptidase in which a polymer carrier and a residue of drug compound are bound to each other by means of a spacer containing an oligopeptide, and measuring a resulting hydrolysate. The present invention was achieved on the basis of these findings.

The present invention thus provides a DDS compound comprising a carboxy($C_{1-4}$)alkyldextran polyalcohol modified with a saccharide compound and a residue of a drug compound bound to the carboxy($C_{1-4}$)alkyldextran polyalcohol.

According to preferred embodiments of the DDS compound, the present invention provides the above DDS compound wherein the carboxy($C_{1-4}$)alkyldextran polyalcohol modified with a saccharide compound and the residue of a drug compound are bound to each other by means of a spacer; the above DDS compound wherein the spacer comprises one amino acid or 2 to 8 amino acids linked by peptide bond(s); the above DDS compound wherein the carboxy($C_{1-4}$)alkyldextran polyalcohol modified with a saccharide compound is formed by binding a saccharide compound and a carboxy($C_{1-4}$)alkyldextran polyalcohol by means of a linker; and the above DDS compound wherein the carboxy($C_{1-4}$) alkyldextran polyalcohol modified with a saccharide compound is a compound with cluster modification by a saccharide compound bound by means of a linker.

The present invention also provides a DDS compound which is obtainable by binding a residue of a drug compound to a carboxy($C_{1-4}$)alkyldextran polyalcohol in which a part of carboxyl groups of the carboxy($C_{1-4}$)alkyl moiety are modified with a saccharide compound.

According to preferred embodiments of the DDS compound, the present invention provides the above DDS compound which is obtainable by binding the carboxy($C_{1-4}$) alkyldextran polyalcohol and the residue of a drug compound by means of a spacer; and the above DDS compound which is obtainable by binding the residue of drug compound to the carboxy($C_{1-4}$)alkyldextran polyalcohol which is produced by binding the saccharide compound or a linker bound to the saccharide compound to a part of carboxyl groups of the carboxy($C_{1-4}$)alkyl moiety of the carboxy($C_{1-4}$)-alkyldextran polyalcohol.

The present invention further provides a DDS compound which is obtainable by modifying, with a saccharide compound, a carboxy($C_{1-4}$)alkyldextran polyalcohol in which a residue of a drug compound is bound to a part of carboxyl groups of the carboxy($C_{1-4}$)alkyl moiety by means of a spacer.

According to preferred embodiments of the aforementioned DDS compound, the present invention provides the above DDS compound which is obtainable by binding the carboxy($C_{1-4}$)alkyldextran polyalcohol and the saccharide compound by means of a linker; and the above DDS compound which is obtainable by modifying, with a saccharide compound, a carboxy($C_{1-4}$)alkyldextran polyalcohol produced by binding a residue of a drug compound to a part of carboxyl groups of the carboxy($C_{1-4}$)alkyl moiety by means of a spacer comprising one amino acid or a spacer comprising 2 to 8 amino acids linked by peptide bond(s).

According to further preferred embodiment of the present invention, there are provided the above DDS compounds wherein the saccharide compound is galactose, galactosamine or derivatives thereof; the above DDS compounds wherein the dextran polyalcohol that constitutes the carboxy ($C_{1-4}$)alkyldextran polyalcohol is a dextran polyalcohol which is obtained by treating a dextran under conditions that enable substantially complete polyalcoholization; the above DDS compounds wherein the carboxy($C_{1-4}$)alkyldextran polyalcohol is carboxymethyldextran polyalcohol; the above DDS compounds wherein substitution degree of galactose or galactosamine or a derivative thereof, or a that of a clustered galactose or galactosamine or a derivative thereof is 0.01 to 1.0 per saccharide residue of the carboxy($C_{1-4}$)alkyldextran polyalcohol; the above DDS compounds wherein the drug compound is an antineoplastic agent or an anti-inflammatory agent; the above DDS compounds wherein the drug compound is (1S,9S)-1-amino-9-ethyl-5-fluoro-2,3-dihydro-9-hydroxy-4-methyl-1H,12H-benzo[de]pyrano[3',4':6,7]indolizino[1,2-b]-quinoline-10,13(9H,15H)-dione; and the above DDS compounds which are a medicament for treating liver cancer.

According to other aspects of the present invention, there are provided a carboxy($C_{1-4}$)alkyldextran polyalcohol modified with a saccharide compound; a polymer carrier comprising a carboxy($C_{1-4}$)alkyldextran polyalcohol modified with a saccharide compound; and a carboxy($C_{1-4}$)alkyldextran polyalcohol modified with a saccharide compound for a use in the manufacture of the above DDS compounds. According to further aspect of the present invention, there is provided a use of a carboxy($C_{1-4}$)alkyldextran polyalcohol modified with a saccharide compound for the manufacture of the above DDS compounds.

According to a still further aspect of the present invention, there is provided a method for measuring a DDS compound in which a polymer carrier and a residue of a drug compound are bound to each other by means of a spacer comprising 2 to 8 amino acids linked by peptide bond(s), which comprises the steps of treating the DDS compound with a peptidase, and measuring a resulting hydrolysate.

According to preferred embodiments of the aforementioned method, there are provided the above method which is used for measurement of the DDS compound contained in a sample from a living body; the above method which is used for measurement of content of the residue of a drug compounds introduced to the DDS compound; the above method wherein the hydrolysate is the drug compound; the above method wherein the hydrolysate is a compound consisting of the residue of a drug compound bound with a part of the spacer; and the above method wherein a part of the spacer is one amino acid derived from the spacer.

According to further preferred embodiments of the aforementioned method of the present invention, there are provided the above method wherein the polymer carrier is those having carboxyl groups, preferably a polysaccharide derivative having carboxyl groups; the above method wherein the polymer carrier is a carboxy($C_{1-4}$)-alkyldextran polyalcohol, preferably carboxymethyldextran polyalcohol; the above method wherein the dextran polyalcohol that constitutes the carboxy($C_{1-4}$)-alkyldextran polyalcohol is a dextran polyalcohol which is obtained by treating a dextran under conditions that enable substantially complete polyalcoholization; the above method wherein the polymer carrier is modified with a saccharide compound; the above method wherein the drug compound introduced to the DDS compound is an antineoplastic agent or an anti-inflammatory agent; the above method wherein the spacer is a tetrapeptide represented as, from the N-terminal, -Gly-Gly-Phe-Gly- (SEQ ID NO. 1) or a tetrapeptid represented as, from the N-terminal, -Gly-Gly-Gly-Phe- (SEQ ID NO. 8); the above method wherein the spacer is a group represented as, from the N-terminal, -Gly-Gly-Phe-Gly-NH—Y'—CH$_2$—O—CO— (SEQ ID NO. 1) or -Gly-Gly-Gly-Phe-NH—Y'—CH$_2$—O—CO— (SEQ ID NO. 8) wherein Y' represents p-phenylene group; the above method wherein the peptidase is α-chymotrypsin or papain; and the above method wherein the drug compound is (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione.

According to a particularly preferred embodiment of the above method of the present invention, the above method can be used for measurement of a DDS compound in which a carboxy($C_{1-4}$)alkyldextran polyalcohol and (1S,9S)-1-amino-9-ethyl-5-fluoro-2,3-dihydro-9-hydroxy-4-methyl-1H,12H-benzo[de]pyrano[3',4':6,7]-indolizino[1,2-b]quinoline-10,13(9H,15H)-dione are bound to each other by means of a spacer comprising a tetrapeptide represented as, from the N-terminal, -Gly-Gly-Phe-Gly- (SEQ ID NO. 1) or a tetrapeptide represented as, from the N-terminal, -Gly-Gly-Gly-Phe- (SEQ ID NO. 8), and the DDS compound or a content of the antineoplastic agent introduced to the DDS compound can be measured by using α-chymotrypsin as the peptidase, and by measuring (1S,9S)-9-ethyl-5-fluoro-1-glycylamino-2,3-dihydro-9-hydroxy-4-methyl-1H,12H-benzo[de]pyrano[3',4':6,7]indolizino[1,2-b]-quinoline-10,13(9H,15H)-dione as the hydrolysate.

BEST MODE FOR CARRYING OUT THE INVENTION

Figure 1:
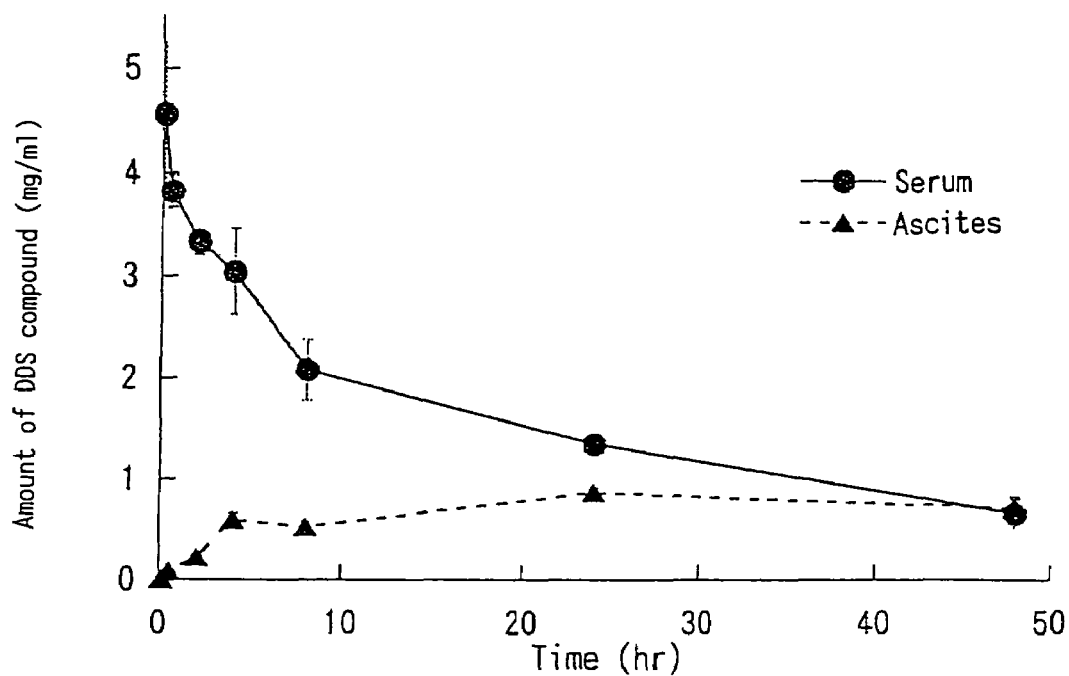
FIG. 1 shows blood and ascites concentrations of DDS compound measured by the method of the present invention (Example 4).

The DDS compound of the present invention is characterized in that it comprises a carboxy($C_{1-4}$)alkyldextran polyalcohol modified with a saccharide compound and a residue of a drug compound bound to the carboxy($C_{1-4}$) alkyldextran polyalcohol. More specifically, the DDS compound of the present invention includes those (1) wherein the carboxy($C_{1-4}$)alkyldextran polyalcohol modified with a saccharide compound and the residue of a drug compound are bound to each other without a spacer, and (2) wherein the carboxy($C_{1-4}$)alkyldextran polyalcohol modified with a saccharide compound and the residue of a drug compound are bound to each other by means of a spacer.

Examples of those wherein the carboxy($C_{1-4}$)alkyldextran polyalcohol modified with a saccharide compound and the residue of a drug compound are bound to each other by means of a spacer include, for example, those wherein the carboxy($C_{1-4}$)alkyldextran polyalcohol modified with a saccharide compound and the residue of drug compound are bound to each other by means of a spacer that comprises one amino acid; those wherein the carboxy($C_{1-4}$)alkyldextran polyalcohol modified with a saccharide compound and the residue of drug compound are bound to each other by means of a spacer that comprises 2 to 8 amino acids linked by peptide bond(s), or a spacer comprising an oligopeptide which comprises 2 to 8 amino acids linked by peptide bond(s) and is bound to a linking group represented by —NH—Y—CO— wherein Y represents an alkylene group having 1 to 8 carbon atoms or —$C_6H_4$—$CH_2$—O— wherein —$C_6H_4$— represents a phenylene group which may have one or more substituents, preferably represents p-phenylene group. The term "modified" used herein should be construed in its broadest sense, which includes modifications with a covalent bond by direct binding of, or indirect binding by means of a linker of a saccharide compound and a carboxy ($C_{1-4}$)alkyldextran polyalcohol, and the term should not be construed as any limiting sense.

The residue of a drug compound contained in the above DDS compound is a main partial structure derived from a drug compound used for therapeutic and/or preventive treatment of diseases of mammals including humans as a medicament, for example, an antineoplastic agent, an anti-inflammatory agent, an antibacterial agent or the like. However, a use of the drug compound from which the residue is derived is not limited to those mentioned above. As the drug compound, any compounds may be used so long as they have one or more reactive functional groups capable of participating in bond formation with a carboxy($C_{1-4}$)alkyldextran polyalcohol or a spacer (for example, amino group, carboxyl group, hydroxyl group, thiol group, ester group or the like). The residue of the drug compound may be bound to either a carboxyl group of the carboxy($C_{1-4}$)alkyldextran polyalcohol or a reactive functional group present in the spacer (for example, when a peptide spacer is used, an N-terminal amino group, a C-terminal carboxyl group, a reactive functional group present in an amino acid constituting the spacer and the like). The term "drug compound" used in the present specification also includes a prodrug compound which contains, as a part thereof, a major structure of a drug compound having pharmacological activity, per se, and can reproduce the compound in vivo.

More specifically, the term "residue of a drug compound" used in the present specification means a partial structure derived from the drug compound existing in the compound after bond formation, assuming that a bond between the carboxy($C_{1-4}$)alkyldextran polyalcohol or the spacer and the residue of a drug compound is formed through a reaction (e.g., dehydration condensation and the like) of a reactive functional group of the drug compound and a reactive functional group of the carboxy($C_{1-4}$)alkyldextran polyalcohol or the spacer. For example, when the drug compound is represented by D-$NH_2$, D-COOH, D-COOR, D-OH, D-SH, D-$CONH_2$, or D-NH—COOR (R is a lower alkyl group or the like), the residue of the drug compound is represented by D-NH-(D-NH—CO-Q etc.), D-CO-(D-CO—NH-Q, D-CO—O-Q, D-CO—S-Q, etc.), D-CO-(D-CO—NH-Q, D-CO—O-Q, D-CO—S-Q, etc.), D-O-(D-O—CO-Q, D-O-Q, etc.), D-S-(D-S—CO-Q, D-S-Q, etc.), D-CONH-(D-CO—NH—CO-Q etc.), and D-NH—CO-(D-NH—CO—O-Q, D-NH—CO—NH-Q, etc.), respectively (the parenthesized formulas represent binding modes between the spacer or the carboxy($C_{1-4}$)alkyldextran polyalcohol and the residue of the drug compound, wherein Q represents a partial structure of the spacer and the carboxy ($C_{1-4}$)alkyldextran polyalcohol excluding a reactive functional group and a carboxyl group, respectively). However, the type of the bond between the spacer or the carboxy($C_{1-4}$)alkyldextran polyalcohol and the residue of the drug compound is not limited to those mentioned above.

As the residue of the drug compound, for example, residues of antineoplastic agents such as doxorubicin, daunorubicin, mitomycin C, bleomycin, cyclocytidine, vincristine, vinblastine, methotrexate, platinum antineoplastic agents (Cisplatin or derivatives thereof), taxol or derivatives thereof, camptothecin or derivatives thereof (antineoplastic agents described in Japanese Patent Unexamined Publication (KOKAI) No. (Hei) 6-87746/1994, preferably (1S,9S)-1-amino-9-ethyl-5-fluoro-2,3-dihydro-9-hydroxy-4-methyl-1H,12H-benzo[de]pyrano[3',4':6,7]indolizino[1,2-b]-quinoline-10,13-(9H,15H)-dione disclosed in claim 2 or the like) may preferably be used. In addition, residues of steroidal anti-inflammatory agents such as hydrocortisone succinate and prednisolone succinate, and nonsteroidal anti-inflammatory agents such as mefenamic acid, flufenamic acid, diclofenac, ibuprofen, and tinoridine are also preferred.

Where a spacer comprising one amino acid or a spacer comprising 2 to 8 amino acids linked by peptide bond(s) is used as the spacer that binds the drug compound to the carboxy($C_{1-4}$)alkyldextran polyalcohol, the spacer has a form of a residue of one amino acid, which means a residue obtained by removing one hydrogen atom and one hydroxyl group from an amino group and a carboxyl group of the amino acid, respectively, or a residue of an oligopeptide comprising 2 to 8 amino acids linked by peptide bond(s), which means a residue obtained by removing one hydrogen atom and one hydroxyl group from the N-terminal amino group and the C-terminal carboxyl group of the oligopeptide, respectively.

Preferred spacers are residues of oligopeptides comprising 2 to 6 amino acids. Kinds of amino acids constituting of the spacer are not particularly limited, and for example, L- or D-amino acids, preferably L-amino acids can be used, and, β-alanine, ε-aminocaproic acid, γ-aminobutyric acid or the like may also be used as well as α-amino acids. These amino acids other than α-amino acids are preferably located close to the polysaccharide compound in the spacer.

For example, where an oligopeptide spacer is used, the bonding direction is not particularly limited, and generally, the N-terminal of the spacer can be bound to a carboxyl group of the carboxy($C_{1-4}$)alkyldextran polyalcohol by means of an acid-amide bond, and the C-terminal of the spacer can be bound to an amino group of the drug compound. Alternatively, for example, where a lysine residue is incorporated as a unit of the peptide spacer, the α-amino group and the ε-amino group of the lysine residue are allowed to form respective acid-amide bonds with carboxyl groups of other amino acids so as to form N-terminals at both ends of the peptide spacer, which enables bond formation with carboxyl groups of the drug compounds. In addition, by incorporating one or more residues of diamine compounds or dicarboxylic acid compounds (residues of diamine compounds such as ethylenediamine or dicarboxylic acid compounds such as succinic acid) as units in a spacer, a spacer having either N-terminals or C-terminals at both ends may be utilized.

Where a spacer comprising an oligopeptide is used, the amino acid sequence thereof is not particularly limited. Preferably used spacers include, for example, a spacer being a residue of a dipeptide represented by —X-Z-, wherein X represents a residue of a hydrophobic amino acid and Z represents a residue of a hydrophilic amino acid; and —X-Z- means a residue which consists of a dipeptide that is formed by a peptide bond between a hydrophobic amino acid (X)

and a hydrophilic amino acid (Z) at the N-terminal side and the C-terminal side, respectively, and whose one hydrogen atom and one hydroxyl group are removed from the amino group at the N-terminal and the carboxyl group at the C-terminal, respectively, and a spacer containing a residue of the dipeptide as a partial peptide sequence. As the hydrophobic amino acid, for example, phenylalanine, tyrosine, leucine or the like can be used, and as the hydrophilic amino acid, for example, glycine, alanine or the like can be used. The spacer may have a repeated sequence of the dipeptide residues (for example, —X-Z-X-Z-, —X-Z-X-Z-X-Z- and the like).

By using the spacer containing such dipeptide structure, the spacer can be hydrolyzed in tumorous sites or inflammatory sites, which is considered abundant in peptidase, to release the drug compound at a high concentration in the sites immediately. Accordingly, the partial structure formed by binding the spacer containing the above dipeptide and the drug compound to each other is a preferred partial structure of the DDS compound according to the present invention. Where a residue of an antineoplastic agent exhibiting antineoplastic activity (e.g., doxorubicin) dependent on the concentration is used as the residue of the drug compound, a spacer composed of the above dipeptide residue represented by —X-Z- or a spacer containing the above dipeptide residue as a partial peptide sequence may be preferably used.

In addition, where a time-dependent type antineoplastic agent which requires a retained working time at over a certain concentration is used as the residue of the drug compound, enhanced antineoplastic activity may sometimes be obtained by using the above spacer. Examples of such an antineoplastic agent include the antineoplastic agents disclosed in the Japanese Patent Unexamined Publication (KOKAI) No. (Hei) 6-87746/1994, preferably the antineoplastic agent disclosed in claim 2. The spacers are not limited to those mentioned above, and it is generally necessary to choose an appropriate spacer from viewpoints of the mode of action of the antineoplastic agent, characteristics in pharmacokinetics or appearance of toxicity, releasability in vivo of the antineoplastic agent and the like. For carcinomas exhibiting rapid proliferation, it is generally preferred to choose the above spacer capable of releasing the drug compound at a high concentration in a short time.

Specific examples of oligopeptides that can be used as the spacer are shown in the following table; however, spacers used for the DDS compounds of the present invention are not limited to those mentioned below. It can be readily understood that one of ordinary skilled in the art can appropriately determine whether or not a spacer is used, or choose the type of a spacer when a spacer is used so as to achieve an optimum releasing rate of a drug compound. In the table, the left ends of peptide sequences are N-terminals and the residues of drug compounds are bound to C-terminals. D-Phe represents the D-phenylalanine residue and the other amino acids represent L-amino acids. The degrees of the releasing rate were judged from the degree of appearance of efficacy of the DDS compounds carrying doxorubicin against Walker 256 tumor-bearing rats, or from free doxorubicin concentrations at tumorous sites of Walker 256 tumor-bearing rats. For doxorubicin, a spacer that can release the drug compound at a high concentration immediately, e.g., -Gly-Gly-Phe-Gly- (SEQ ID NO. 1), is preferably used among the listed spacers.

TABLE 1

| (a) Spacers having high releasing rate | |
|---|---|
| -Leu-Gly- | |
| -Tyr-Gly- | |
| -Phe-Gly- | |
| -Gly-Phe-Gly- | |
| -Gly-Gly-Phe-Gly- | (SEQ ID NO. 1) |
| -Gly-Phe-Gly-Gly- | (SEQ ID NO. 2) |
| -Phe-Gly-Gly-Gly- | (SEQ ID NO. 3) |
| -Phe-Phe-Gly-Gly- | (SEQ ID NO. 4) |
| -Gly-Gly-Gly-Phe-Gly- | (SEQ ID NO. 5) |
| (b) Spacers having relatively high releasing rate | |
| -Gly-Gly-Phe-Phe- | (SEQ ID NO. 6) |
| -Gly-Gly-Gly-Gly-Gly-Gly- | (SEQ ID NO. 7) |
| (c) Spacers having relatively low releasing rate | |
| -Phe-Phe- | |
| -Ala-Gly- | |
| -Pro-Gly- | |
| -Gly-Gly-Gly-Phe- | (SEQ ID NO. 8) |
| (d) Spacers having low releasing rate | |
| -Gly- | |
| -D-Phe-Gly- | |
| -Gly-Phe- | |
| -Ser-Gly- | |
| -Gly-Gly- | |
| -Gly-Gly-Gly- | |
| -Gly-Gly-Gly-Gly- | (SEQ ID NO. 9) |

The DDS compound of the present invention is characterized to have a carboxy($C_{1-4}$)alkyldextran polyalcohol modified with a saccharide compound as a polymer carrier. The degree of polyalcoholization of the carboxy($C_{1-4}$)alkyldextran polyalcohol contained in the DDS compound of the present invention is not particularly limited. Preferably, dextran polyalcohols constituting the carboxy($C_{1-4}$)alkyldextran polyalcohol may be those obtained by treating a dextran under a condition which enables substantially complete polyalcoholization.

The sort of the dextran used for the preparation of the carboxy($C_{1-4}$)alkyldextran polyalcohol is not particularly limited, and the dextran may contain α-D-1,6-linkages at any rate. For example, dextran containing α-D-1,6-linkages at a rate of 85% or more, 90% or more, or 95% or more can be used. The molecular weight of the dextran is not particularly limited, and for example, dextran having a molecular weight of from about 1,000 to about 2,000,000, preferably from about 3,000 to about 800,000 can be used. As the $C_{1-4}$ alkyl group constituting the carboxy($C_{1-4}$)alkyl group of the carboxy($C_{1-4}$)alkyldextran polyalcohol, a linear or branched $C_{1-4}$ alkyl group, specifically, methyl group, ethyl group, n-propyl group, isopropyl group, n-butyl group, sec-butyl group or the like can be used, and methyl group can preferably be used.

When dextran is used as a starting material, the dextran can be treated successively with a large excess amount of sodium periodate and sodium borohydride to obtain a dextran polyalcohol subjected to substantially complete polyalcoholization. However, the method for the polyalcoholization of dextran is not limited to the method mentioned above, and any method available to those skilled in the art may be utilized. The carboxy($C_{1-4}$)alkylation can be carried out, for example, by reacting a halogenated ($C_{1-4}$)alkylcarboxylic acid such as chloroacetic acid, bromoacetic acid, α-chloropropionic acid, α-methyl-α-chloropropionic acid, β-chloropropionic acid, α-methyl-β-chloropropionic acid, α-chlorobutyric acid, β-chlorobutyric acid, or γ-chlorobutyric acid, preferably chloroacetic acid, with hydroxyl groups of the dextran polyalcohol to achieve partial or complete carboxy($C_{1-4}$)alkylation of the hydroxyl groups.

For example, the dextran polyalcohol is dissolved in an inert solvent which does not participate in the reactions (e.g., water, N,N-dimethylformamide, or dimethyl sulfoxide), and the resulting solution is added with a halogenated ($C_{1-4}$) alkylcarboxylic acid or a salt thereof in the presence of a base (e.g., sodium hydroxide or potassium hydroxide), and then the mixture is allowed to react for several minutes to several days at a temperature under ice-cooling to about 100° C. The degree of introduction of the carboxy($C_{1-4}$)alkyl group may be easily controlled, for example, by suitably choosing the reaction temperature of the carboxy($C_{1-4}$) alkylation or the amount of the halogenated ($C_{1-4}$)alkyl carboxylic acid or bases used as reagents, and these means are well-known to those skilled in the art. The degree of the carboxy($C_{1-4}$)alkylation based on one sugar residue of the dextran polyalcohol is not particularly limited, and for example, the degree may be in the range of from 0.01 to 2.0, preferably from 0.1 to 1.0.

Kinds of the saccharide compound used for the modification of the carboxy($C_{1-4}$)alkyldextran polyalcohol are not particularly limited, and those skilled in the art can appropriately choose the saccharide compound depending on the type of an organ to be a target of the DDS compound, pharmacokinetics and the like. As the saccharide compound, any of monosaccharides, oligosaccharides, and derivatives thereof may be used. Furthermore, kinds of a bond between the saccharide compound and the carboxy($C_{1-4}$)alkyldextran polyalcohol are not particularly limited. The saccharide compound and the carboxy($C_{1-4}$)alkyldextran polyalcohol may be, for example, directly bound through an O-α-glycosidic linkage or O-β-glycosidic linkage, or the both may be bound to each other by means of an appropriate linker. The term "linker" used herein must be construed in its broadest sense so as to include any linkers that can be used for the binding between the saccharide compound residue and the carboxy($C_{1-4}$)alkyldextran polyalcohol. The amount of the saccharide compound introduced to the carboxy($C_{1-4}$)alkyldextran polyalcohol (degree of substitution) is not particularly limited, and the amount can suitably be chosen depending on various conditions such as the kind of the saccharide compound, desired degree of selectivity, and the kind of the drug compound. The amount may generally be about 0.01 to about 1.0 per saccharide residue of the carboxy($C_{1-4}$)alkyldextran polyalcohol.

When a linker is used, kinds of the linker are not particularly limited. It is preferable to use, for example, a linker represented by —O—($CH_2$)$_n$—NH— (n is an integer of from 1 to 16) or —(O—$CH_2CH_2$)$_m$—NH— (m is an integer of from 1 to 10). The carboxy($C_{1-4}$)alkyldextran polyalcohol can be modified with a saccharide compound by binding the O-terminal or the N-terminal, preferably the N-terminal of the aforementioned linker to a saccharide compound by means of an O-α-glycosidic linkage or O-β-glycosidic linkage, and binding the other end of the linker to a carboxyl group of the carboxy($C_{1-4}$)alkyldextran polyalcohol by means of an amide bond or an ester bond.

It is also possible to produce a cluster-modified compound by using a linker suitable for the so-called cluster modification. The cluster-modified compounds are those with a bunch of saccharide compounds attached to the carboxyl group of the carboxy($C_{1-4}$)alkyldextran polyalcohol by means of a linker suitable for the cluster modification, and specific means for their manufacture are disclosed in, for example, Japanese Patent Nos. 2774417, 2774429, Biol. Pharm. Bull., 20, pp. 259–266, 1997 and the like. In the cluster-modified compound, plural saccharide compounds are located in a certain limited space, thereby the compound has characteristic features of enhanced affinity for a receptor and an excellent organ selectivity. An example of the cluster modification in the DDS compound of the present invention is shown below (in the following formula, a partial structure of the carboxy($C_{1-4}$)alkyldextran polyalcohol molecule modified with a cluster is shown, and a residue of the drug compound is omitted). However, the mode of the cluster modification used for the DDS compound of the present invention is not limited to the following example, and it should be understood that any appropriate means can be selected by those skilled in the art.

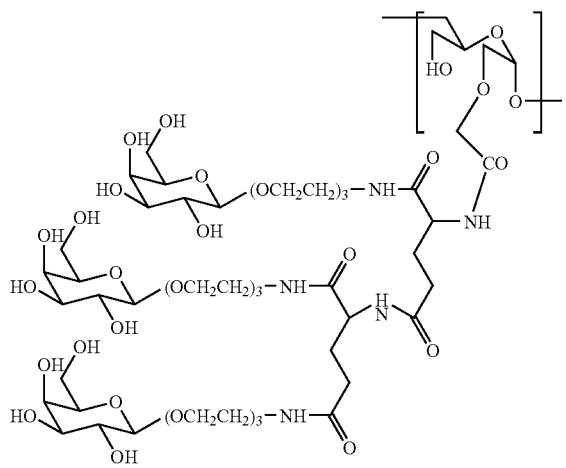

Examples of the monosaccharides include, for example, hexoses such as glucose, fructose, mannose, galactose, fucose, neuraminic acid and uronic acid; hexosamines such as galactosamine and glucosamine; pentoses such as ribose, deoxyribose, arabinose and xylose and the like. As the derivatives thereof, for example, N- or O-acyl derivatives, O-alkyl derivative, sulfuric acid esters, phosphoric acid esters thereof and the like may be used. More specific examples of the derivatives of monosaccharides include N-acetylneuraminic acid, N-acetylgalactosamine, N-acetylglucosamine, mannose-6-phosphate, galactose-3-phosphate, 6-O-benzoylglucose, 6-O-carboxymethyl-N-acetylglucosamine, 2-N-benzylglucosamine and the like. As the oligosaccharides, for example, linear or, blanched heterooligosaccharide or homooligosaccharides constituted by the aforementioned monosaccharides or derivatives thereof can be used. More specifically, sucrose, sialyl Lewis A, sialyl Lewis X, lactose, maltose, Lewis X, sulfated Lewis X and the like may be used. Among them, as the saccharide compound which enhances liver selectivity, galactose or galactosamine or derivatives thereof, and oligosaccharides which has galactose or N-acetylgalactosamine at the non-reducing terminal (e.g., lactose) are preferred, and galactose and N-acetylgalactosamine are particularly preferred.

Methods for producing the DDS compound of the present invention are not particularly limited. General manufacturing processes are shown below, and their specific examples will be detailed in the examples in the specification. Those skilled in the art can readily manufacture a DDS compound that falls within the scope of the present invention by referring to the general explanation set out below and preparation methods described in the examples, and by appropriately choosing starting materials, reagents, reaction conditions and the like, and if necessary, by modifying and altering the methods. In general, the DDS compound of the present invention can be produced by modifying a carboxy ($C_{1-4}$)alkyldextran polyalcohol with a saccharide compound according to a suitable method, and allowing the modified compound to react with the residue of the drug compound, or with a spacer that is bound to a residue of drug compound. A carboxy($C_{1-4}$)alkyldextran polyalcohol can be generally prepared in the form of an aqueous solution of an alkali metal salt such as sodium salt or potassium salt, and the modification with a saccharide compound and the reaction with a drug compound (or a spacer bound to the drug compound) can be performed in water or an organic solvent containing water.

Alternatively, a carboxy($C_{1-4}$)alkyldextran polyalcohol or a carboxy($C_{1-4}$)alkyldextran polyalcohol modified with a saccharide compound may be converted into an organic amine salt, and subsequent reactions may be performed in an organic solvent which is substantially free from water. As the organic amine salt, for example, salts of aliphatic amines such as triethylamine, trimethylamine, or triethanolamine; salts of alicyclic and aromatic amines such as N-methylpyrrolidine, N-methylpiperidine, N-methylmorpholine, or dimethyl-aminopyridine; or quaternary ammonium salts such as tetramethylammonium chloride or tetraethylammonium chloride can be used. The conversion from the sodium salt of the carboxy($C_{1-4}$)alkyldextran polyalcohol or the carboxy ($C_{1-4}$)alkyldextran polyalcohol modified with a saccharide compound into a corresponding organic amine salt can be carried out by using an ion exchange resin or the like. For example, a sodium salt of a carboxymethyldextran polyalcohol or a saccharide-modified compound thereof may be dissolved in water, applied to a column charged with Bio-Rad AG50W-X2 (200–400 mesh, $H^+$ type) resin, and eluted with water, and then the resulting effluent can be added with an organic amine such as triethylamine and lyophilized. Alternatively, it is also possible to carry out the conversion by one step, i.e., by dissolving a sodium salt of a carboxymethyldextran polyalcohol or a saccharide-modified compound thereof in water and then passing the solution through a triethylammonium type resin.

The bond between the drug compound, per se, and a carboxyl group of the carboxy($C_{1-4}$)alkyldextran polyalcohol, or the bond between the spacer bound to the drug compound and a carboxyl group of the carboxy($C_{1-4}$)alkyldextran polyalcohol can generally be formed by binding a reactive amino group of the drug compound, per se, or a reactive amino group of the spacer (N-terminal amino group or the like in a peptide spacer) to a carboxyl group of the carboxy($C_{1-4}$)alkyldextran polyalcohol by means of an acid-amide bond. However, the bond between the drug compound or the spacer and the carboxyl group of the carboxy($C_{1-4}$) alkyldextran polyalcohol is not limited to the above-described bond, and other chemical bonds and linkages utilizing one or more spacers may be used. For example, an acid anhydride may be formed between a C-terminal carboxyl group of a peptide spacer or a carboxyl group of the drug compound and a carboxyl group of the carboxy($C_{1-4}$)alkyldextran polyalcohol, or by using a diamine compound such as ethylenediamine used as a spacer, each of the carboxyl groups may be bound by means of an acid-amide bond to each of amino groups of the diamine compound.

When a reactive amino group of a drug compound, per se, or the N-terminal amino group of a spacer is bound to a carboxyl group of the carboxymethyldextran polyalcohol by means of an acid-amide bond, dehydration condensation agents ordinarily used for synthesis of peptide chains, for example, N,N'-dicycloalkylcarbodiimides such as N,N'-dicyclohexylcarbodiimide (DCC), carbodiimide derivatives such as 1-ethyl-3-(3-dimethylaminopropyl)carbodiimide (EDAPC), 1-ethoxycarbonyl-2-ethoxy-1,2-dihydroxyquinoline (EEDQ) and the like can be used. In this case, benzotriazole derivatives such as 1-hydroxybenzotriazole (HOBT) may be added as required. In addition, the reaction may also be performed by the activated ester method or the acid halide method.

When the reaction is performed in a non-aqueous system, any organic solvents may be used so long as they are substantially free from water and can dissolve the reactants (an organic amine salt of a carboxymethyldextran polyalcohol modified with a saccharide compound and a drug compound or a spacer bound to a drug compound and the like). For example, N,N-dimethylformamide, dimethyl sulfoxide, acetamide, N-methylpyrrolidone, sulfolane and the like can preferably be used. Although the amount of the residue of the drug compound which is introduced into the carboxy($C_{1-4}$)alkyldextran polyalcohol modified with a saccharide compound is not particularly limited, the amount should be suitably chosen depending on the sort of the residue of a drug compound, and from the viewpoints of pharmacokinetics, efficacy, and toxicity of the DDS compound. Generally, the range of approximately from 0.1 to 30% by weight, preferably approximately from 2 to 15% by weight can be chosen. When the antineoplastic agent disclosed in claim 2 of the Japanese Patent Unexamined Publication (KOKAI) No. (Hei) 6-87746/1994 is used as the drug compound, the amount of the drug compound to be introduced may be, for example, about 1 to 15% by weight, preferably about 4 to 8% by weight. The ratio of residues of the drug compound introduced to the carboxy($C_{1-4}$)alkyldextran polyalcohol can be easily determined by, for example, absorption spectrometric analysis.

For example, as for the antineoplastic agent disclosed in claim 2 of the Japanese Patent Unexamined Publication (KOKAI) No. (Hei) 6-87746/1994 is used as the drug compound, it is known that the equilibrium of the drug compound lies to the compound whose lactone ring is closed (the ring-closed compound) in an acidic aqueous medium (for example, approximately at pH 3), whereas the equilibrium lies to the compound whose lactone ring is opened (the ring-opened compound) in a basic aqueous medium (for example, approximately at pH 10). The DDS compounds introduced with the residue corresponding to each of the ring-closed and ring-opened compounds have similar antineoplastic activity. However, when a reactant in the form of the ring-opened compound is present and the carboxy($C_{1-4}$)alkyldextran polyalcohol modified with a saccharide compound is reacted with the spacer bound to the aforementioned drug compound (e.g., an oligopeptide spacer), a condensation reaction will proceed between a carboxyl group derived from the lactone ring and an amino group derived from the spacer. Due to the side reaction, a yield may significantly be decreased, and moreover, a desired DDS compound cannot sometimes be uniformly obtained. Such side reaction can be avoided by using the ring-closed compound as a reactant in a non-aqueous system that does not allow the equilibrium.

The DDS compound of the present invention is characterized in that it can specifically exhibit desired pharmacological activity at a local site such as tumorous sites or inflammatory sites depending on the sort of a residue of a drug compound (e.g., residues of drug compounds such as antineoplastic agents or anti-inflammatory agents), and can reduce toxicity inherent to the drug compound, per se. Furthermore, the DDS compound of the present invention also has excellent blood vessel permeability. Since protease (peptidase) is expressed at tumorous sites or inflammatory sites, the DDS compound having a spacer comprising an oligopeptide is readily hydrolyzed at the spacer moiety to allow the released drug compound to be incorporated into cells and exhibit its efficacy, or the DDS compound is taken into the cells with the aid of a receptor present in a target cell which recognizes the saccharide, and the drug compound released by the action of a protease exhibits its efficacy.

The carboxy($C_{1-4}$)alkyldextran polyalcohol is hardly recognized as an exogenous macromolecule in living bodies, for example, in liver, spleen, bone marrow and the like, and for this reason, the compound distributes to these kinds of organ insufficiently. Whilst, depending on the kind of the saccharide compound, the compound can be distributed at a high concentration in organs abundant in saccharide receptors for the saccharide compound. For example, a DDS compound of the present invention which comprises a carboxy($C_{1-4}$)alkyldextran polyalcohol modified with galactose has excellent liver selectivity. Therefore, the DDS compound that is bound to an antineoplastic agent as the drug compound is useful for the treatment of liver cancer.

A medicament comprising the DDS compound of the present invention may generally be filled in vials or the like in the form of a lyophilized product or other, and provided for clinical use as preparations for parenteral administration such as injections or drip infusions which are dissolved upon use. However, the form of pharmaceutical preparations of the medicament is not limited to the aforementioned forms. For the manufacture of the aforementioned pharmaceutical preparations, pharmaceutical additives available in the field of the art, for example, solubilizers, pH modifiers, stabilizers and the like, can be used, and the pharmaceutical preparation can be prepared as a pharmaceutical composition. Although the dose of the above medicament is not particularly limited, it should normally be decided in view of the dose of the drug compound that constitutes the residue of the drug compound, the amount of the residue of the drug compound introduced into the DDS compound, the condition of a patient, the sort of a disease and the like. For example, where a DDS compound introduced with about 6% by weight of the residue of the antineoplastic agent mentioned in claim 2 of Japanese Patent Unexamined Publication (KOKAI) No. (Hei) 6-87746/1994 is parenterally administered, about 0.1 to 100 mg, preferably about 1 to 30 mg per $m^2$ of body surface area per day may generally be administered once a day, and the administration may preferably repeated every 3 to 4 weeks.

According to another aspect of the present invention, there is provided a method for measuring a DDS compound in which a polymer carrier and a residue of a drug compound are bound to each other by means of a spacer that comprises 2 to 8 amino acids linked by peptide bond(s), which comprises the step of treating the DDS compound with a peptidase, and measuring the resulting hydrolysate.

The term "measurement" used herein should be construed in its broadest sense including measurements performed for quantitative and qualitative determinations. The term preferably means quantitative measurement. The DDS compounds to be measured by the measurement method of the present invention are those comprising a polymer carrier and a residue of drug compound bound to each other by means of a spacer that comprises 2 to 8 amino acids linked by peptide bond(s), and the compound should not be construed in any limitative way. Examples of the spacer comprising 2 to 8 amino acids linked by peptide bond(s) include, for example, a spacer consisting essentially of 2 to 8 amino acids linked by peptide bond(s), as well as a spacer which comprises an oligopeptide consisting of 2 to 8 amino acids linked by peptide bond(s) and said oligopeptide is bound to a bridging group represented by —NH—Y—CO— wherein Y represents a bridging group such as an alkylene group having 1 to 8 carbon atoms or —$C_6H_4$—$CH_2$—O— wherein —$C_6H_4$ represents a phenylene group which may have one or more substituents, preferably represents p-phenylene group. The measuring method of the present invention can be used for, for example, measurement of a concentration of the DDS compound, per se, contained in biological samples such as blood or body fluids. The method of the present invention can also be used for measurement of amount of residue of a drug compounds introduced into a DDS compound (for example, weight % of the residue of a drug compounds relative to the total weight of the DDS compound or the like).

The residue of drug compound contained in the DDS compound to be measured by the method of the present invention has the same meaning as that explained above. Any drug compound may be used so long as they have one or more functional groups capable of binding to the spacer (for example, amino group, carboxyl group, hydroxyl group, thiol group, ester group etc.). The residue of drug compound may be bound to the N-terminal amino group or the C-terminal carboxyl group of the spacer, or a reactive functional group present in an amino acid that constitutes the spacer.

Specific examples of the residue of drug compound are same as those explained for the DDS compounds comprising a carboxy($C_{1-4}$)alkyldextran polyalcohol modified with a saccharide compound and a residue of drug compound bound to each other by means of a spacer. Preferred residues of the drug compounds are also the same as those explained above.

The residue of drug compound contained in the DDS compound to be measured by the method of the present invention binds to a polymer carrier by means of a spacer. A preferred spacer is a residue of oligopeptide that consists of 2 to 8 amino acids linked by peptide bond(s), or a spacer comprising 2 to 8 amino acids linked by peptide bond(s) which is bound to a bridging group represented by —NH—Y'—$CH_2$—O—CO— wherein Y' represents p-phenylene group. The kind of amino acids constituting the spacer, bonding direction of the spacer, amino acid sequences, specific examples thereof and the like are the same as those explained for the DDS compounds comprising a carboxy ($C_{1-4}$)alkyldextran polyalcohol modified with a saccharide compound and a residue of drug compound bound to each other by means of a spacer.

As the polymer carrier that constitutes the DDS compound to be measured by the method of the present invention, for example, synthetic polymers and the like may be used as well as the polysaccharide derivatives. Any polysaccharide derivatives and synthetic polymers may be used so long as they do not exhibit substantial toxicity against living bodies, and they can function as a drug carrier. For example, any polysaccharide derivatives and synthetic polymers that have conventionally been used for the production of DDS compounds can be utilized as the polymer carrier. For example, polysaccharide derivatives having carboxyl groups can preferably be used, and polyalcoholized polysaccharide derivatives can most preferably be used. Examples of the synthetic polymer include, for example, polyethylene glycols; polyamino acids such as polyglutamic acids, polyaspartic acids and polylysines; derivatives of polyvinyl compounds such as N-(2-hydroxypropyl)-methacrylamide derivatives.

More specifically, as the polysaccharide derivatives having carboxyl groups, for example, polysaccharides and derivatives thereof that are chemically or biologically modified can be used, and those having carboxyl groups in their molecules can preferably be used. As examples of the polymer carrier having carboxyl groups in the molecule, polysaccharides such as hyaluronic acid, pectic acid, alginic acid, chondroitin, and heparin; and polysaccharides such as pullulan, dextran, mannan, chitin, inulin, levan, xylan, araban, mannoglucan, and chitosan in which all or a part of hydroxyl groups are introduced with functional groups having a carboxyl group can be used. For example, those having carboxy($C_{1-4}$)alkylated hydroxyl groups or those having hydroxyl groups esterified with one of carboxyl groups of a polybasic acid can preferably be used. In addition, those obtained by polyalcoholizing the above polysaccharides and then introducing functional groups having a carboxyl group may also be used.

A DDS compound using a carboxy($C_{1-4}$)alkyldextran polyalcohol as the polymer carrier is a particularly preferred measuring object according to the method of the present invention. The polyalcoholization degree of the carboxy($C_{1-4}$)alkyldextran polyalcohol, the kinds of dextran used for the manufacture thereof, the manufacturing process and the like are the same as those explained for the DDS compound comprising a carboxy($C_{1-4}$)alkyldextran polyalcohol modified with a saccharide compound and a residue of drug compound bound to each other by means of a spacer.

In addition, a DDS compound using a polymer carrier modified with a saccharide compound as the polymer carrier is also a preferred object for the measurement method of the present invention. For example, a carboxy($C_{1-4}$)alkyldextran polyalcohol modified with a saccharide compound can suitably be used as the polymer carrier. The method for modifying a polymer carrier with a saccharide compound, the kind of the saccharide compound and the like are the same as those explained for the carboxy($C_{1-4}$)alkyldextran polyalcohol modified with a saccharide compound.

The object of the measurement method of the present invention may be a DDS compound produced by using a linker suitable for the so-called cluster modification (so-called cluster-modified compound). The concept of the cluster modification is the same as that explained for the carboxy($C_{1-4}$)alkyldextran polyalcohol modified with a saccharide compound.

The method of the present invention is characterized in that a hydrolysate is measured that is obtained by subjecting a DDS compound to a treatment with a peptidase for the measurement of the DDS compound. Kinds of the peptidase are not particularly limited so long as they can hydrolyze the oligopeptide moiety (an oligopeptide moiety comprising 2 to 8 amino acids linked by peptide bond(s)) contained in the spacer of the DDS compound. For example, subtilisin, α-chymotrypsin, type IV collagenase, pepsine, thermolysin, papain, elastase and the like can be used. Among them, α-chymotrypsin and papain are preferred.

Although types of the hydrolysate are not particularly limited, those detectable by ordinary spectrophotometric techniques such as those utilizing ultraviolet absorption spectrum and fluorescence spectrum are preferred. Generally, the drug compound, per se, may be detected, as well as a compound comprising a part of the spacer that remains and binds to the residue of a drug compound, for example, a drug compound to which one amino acid derived from the spacer is bound, a drug compound to which an oligopeptide consisting of 2 to 8 amino acids derived from the spacer is bound, a drug compound to which one amino acid or the aforementioned oligopeptide derived from the spacer is bound by means of a bridging group represented by —NH—Y—CO— wherein Y represents an alkylene group having 1 to 8 carbon atoms or a group represented by —$C_6H_4$—$CH_2$—O— wherein —$C_6H_4$— represents a phenylene group which may have one or more substituents, preferably represents p-phenylene group. As for the aforementioned hydrolysate, a part or all of reactive functional groups of the drug compound may be hydrolyzed. A desired hydrolysate can be measured by suitably choosing a peptidase depending on the sort of the DDS compound,.

As a sample for the measurement, samples from living bodies which are collected from animals including humans administered with a DDS compound, such as blood, lymph, saliva, urine, feces and extracted tissue can be used, as well as an aqueous solution of DDS compound or a solution of DDS compound in an aqueous organic solvent that does not substantially inhibit the enzymatic reaction. Suitable conditions have been known in the art for various peptidases, and those skilled in the art can readily choose suitable reaction conditions such as a substrate concentration, pH, a buffering agent, a reaction temperature, and a reaction time depending on the kind of the peptidase. Usually, the sample is subjected to a pretreatment such as homogenization and deproteinization, then a peptidase is added to a reaction mixture after dilution so as to have a desired concentration of a DDS compound as a substrate, and the reaction can be continued until the DDS compound is completely hydrolyzed.

The method for measuring the hydrolysate is not particularly limited. When the DDS compound or the amount of an introduced drug compound is quantitatively measured, it is desirable to use ordinary spectrophotometric techniques such as those based on ultraviolet absorption spectrum measurement and fluorescence spectrum measurement, which are used alone or in combination. The measurement may be performed by optionally applying a separation such as by using a high performance liquid chromatography. An accurate quantitative measurement can be performed by preparing a calibration curve beforehand in a measurement system. Typical examples of the method of the present invention are specifically described in detail in the examples of the specification, and accordingly, those skilled in the art can readily carry out the method of the present invention by referring to the above general explanation and specific explanation in the examples, and if necessary, by adding modifications or alterations to the disclosed methods.

EXAMPLES

The present invention will be explained more specifically by examples; however, the scope of the present invention is not limited to the following examples.

Example 1

A DDS compound (Compound 1) in which a carboxymethyldextran polyalcohol (occasionally abbreviated as "CM-Dex-PA" or "CM-dextran polyalcohol" hereinafter in the examples) as a polymer carrier and an antineoplastic agent ((1S,9S)-1-amino-9-ethyl-5-fluoro-2,3-dihydro-9-hydroxy-4-methyl-1H,12H-benzo[de]-pyrano[3',4':6,7]indolizino[1,2-b]quinoline-10,13(9H,15H)-dione disclosed in claim 2 of Japanese Patent Unexamined Publication (KOKAI) (Hei) No. 6-87746/1994 (abbreviated as "DX-8951" in hereinafter in the examples) were bound by means of a tetrapeptide spacer represented as -Gly-Gly-Phe-Gly- (SEQ ID NO. 1) (the oligopeptide is shown as the sequence from their N-terminals, and others are shown in the same manner hereinafter in the examples) was produced according to the method described in Example 15 of International Publication WO97/46260. As the CM-Dex-PA, that having an average molecular weight of 228K, and a carboxymethylation degree (degree of substitution with carboxymethyl groups per constitutional saccharide residue) of 0.4 was used.

10 μl of a solution of the above DDS compound prepared as 400 μg/ml in distilled water was added to 180 μl of Britton Robinson buffer (pH 6.0), and the mixture was further added with 10 μl of an α-chymotrypsin solution prepared as 10 mg/ml in distilled water. The reaction mixture was incubated at 40° C. for 2 hours, and added with 200 μl of 0.5 N HCl solution containing 50% of acetonitrile, and the released hydrolysate (a compound in which glycine derived form the spacer was bound to the amino group of DX-8951 by a peptide bond, which is the compound mentioned in Example 50 of International Publication WO97/46260, abbreviated as "G-DX-8951" hereinafter in the examples) was quantified by HPLC. For the HPLC analysis, a Symmetry C18 (4.6× 100 mm; 3.5 μm, Waters Co.) column was used, and the elution was performed with 0.1 M sodium acetate (pH 5.0) containing 36.5% of organic solvent (methanol:acetonitrile=1:2), and the hydrolysate was detected by fluorescent spectroscopy (Ex. 375 nm and Em. 445 nm). As a result, the DX-8951 content of the aforementioned DDS compound was found to be 5.7%. On the other hand, the DX-8951 content of the aforementioned DDS compound was calculated to be 4.9% based on UV absorption (366 nm) of DX-8951 measured by a spectrophotometer.

Example 2

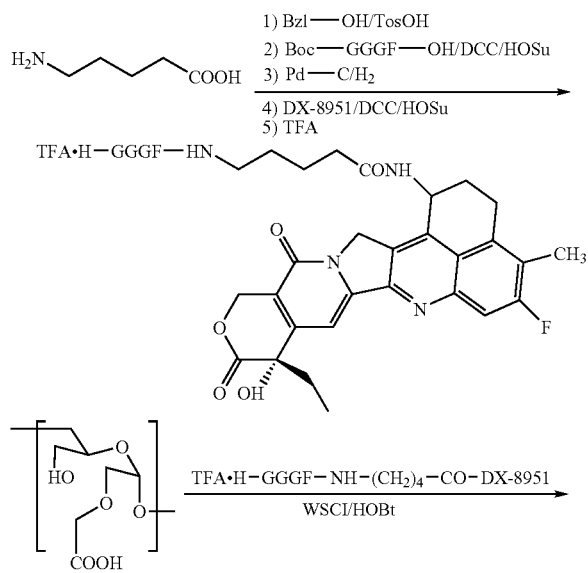

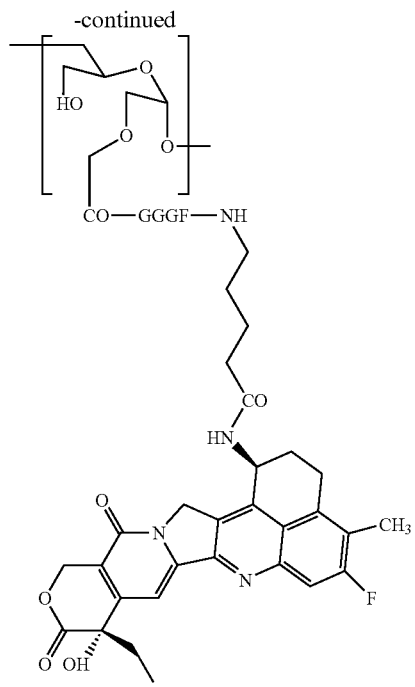

A DDS compound (Compound 2) in which CM-Dex-PA and DX-8951 were bound by means of a spacer represented by -Gly-Gly-Gly-Phe-NH—$(CH_2)_4$—CO— (SEQ ID NO. 8) was prepared as follows. 5-Aminopentanoic acid (1.0 g), p-toluenesulfonic acid (1.95 g), and benzyl alcohol (5 ml) were allowed to react in toluene (50 ml) at 140° C. for 5 hours while removing the produced water by using a Dean-Stark apparatus. The reaction mixture was concentrated, and the resulting residue was solidified by adding ether. The solid obtained was filtrated, washed with ether, and dried to obtain 2.9 g of tosylic acid salt of 5-aminopentanoic acid benzyl ester.

Boc-Gly-Gly-Gly-Phe-OH (575 mg) (SEQ ID NO. 8), HOSu (182 mg), and DCC (326 mg) were dissolved in DMF (20 ml), and the mixture was stirred for 30 minutes. The solution was added with a solution of p-toluenesulfonic acid salt of 5-aminopentanoic acid benzyl ester (500 mg) and triethylamine (0.184 ml) dissolved in DMF (10 ml), and the mixture was stirred for 3 days at room temperature. The reaction mixture was concentrated, and the residue was purified by column chromatography ($CH_2Cl_2$:MeOH=20:1) to obtain 380 mg of Boc-Gly-Gly-Gly-Phe-NH—$(CH_2)_4$—COOBzl (Bzl represents benzyl group) (SEQ ID NO. 8). The Boc-Gly-Gly-Gly-Phe-NH—$(CH_2)_4$—COOBzl (SEQ ID NO. 8) (380 mg) was dissolved in methanol containing 50% of water (20 ml), and the solution was added with 5% Pd—C (water content; 50%, 300 mg) and stirred overnight under hydrogen at ordinary pressure. The catalyst in the reaction mixture was removed by filtration, and the filtrate was concentrated to dryness to obtain Boc-Gly-Gly-Gly-Phe-NH—$(CH_2)_4$—COOH (SEQ ID NO. 8) (330 mg).

The Boc-Gly-Gly-Gly-Phe-NH—$(CH_2)_4$—COOH (SEQ ID NO. 8) (150 mg), DCC (70 mg) and HOSu (40 mg) were dissolved in DMF, and the solution was stirred for 30 minutes. A solution of DX-8951 (160 mg) and triethylamine (0.04 ml) dissolved in DMF was added to the above solution, and then the mixture was stirred overnight at room temperature. The reaction mixture was concentrated, and the resulting residue was purified by column chromatography (CH$_2$Cl$_2$:MeOH=20:1) to obtain Boc-Gly-Gly-Gly-Phe-NH—(CH$_2$)$_4$—CO-DX-8951 (SEQ ID NO. 8) (110 mg). The Boc-Gly-Gly-Gly-Phe-NH—(CH$_2$)$_4$—CO-DX-8951 (SEQ ID NO. 8) (110 mg) was dissolved in TFA (2 ml), and the solution was allowed to react for 1 hour. The reaction mixture was concentrated, and the resulting residue was solidified by addition of ether. The supernatant was removed, and the solid was dried to obtain 100 mg of trifluoroacetic acid salt of H-Gly-Gly-Gly-Phe-NH—(CH$_2$)$_4$—CO-DX-8951 (SEQ ID NO. 8).

$^1$H-NMR (DMSO-d$_6$): δ 8.45–8.55 (m, 2H), 8.28–8.35 (m, 2H), 7.95–8.10 (br, 2H), 7.79 (d, 1H, J=10.7 Hz), 7.70–7.75 (m, 1H), 7.32 (s, 1H), 7.20–7.30 (m, 5H), 7.15–725 (m, 4H), 6.50–6.60 (br, 1H), 5.50–5.60 (m, 1H), 5.40–5.50 (m, 2H), 5.18 (s, 2H), 4.50–4.60 (m, 1H), 3.55–3.95 (m, 7H), 3.00–3.25 (m, 5H), 2.75–2.85 (m, 1H), 2.50 (s, 3H), 2.15–2.25 (m, 4H), 1.86–2.00 (m, 2H), 1.55–1.65 (m, 2H), 1.45–1.55 (m, 2H), 0.88 (t, 3H, J=7.35 Hz)

CM-Dex-PA (350 mg) produced by the method described in Example 13 of WO 97/46260, having an average molecular weight of 337K and a carboxymethylation degree (degree of substitution with carboxymethyl groups per constitutional saccharide residue) of 0.4, was dissolved in water (10 ml). To this solution, a solution of trifluoroacetic acid salt of H-Gly-Gly-Gly-Phe-NH—(CH$_2$)$_4$—CO-DX-8951 (SEQ ID NO. 8) (50 mg) dissolved in methanol (10 ml) was added, and the mixture was further added with a solution of HOBt (7 mg) dissolved in methanol (5 ml). The reaction mixture was adjusted to pH 7.0, added with water-soluble carbodiimide (10 mg), and then the mixture was stirred for 14 hours. The reaction mixture was further added with water-soluble carbodiimide (10 mg), stirred for 2 hours, and then added with water-soluble carbodiimide (10 mg) and stirred for 2 hours. The reaction mixture was diluted with ultrapure water, and the low molecular weight substances were removed by using an ultrafiltration membrane (50K). The filtrate was lyophilized, and the resulting powder was dissolved in 3 M aqueous NaCl, and the solution was added dropwise to ethanol. The deposited solid was separated by centrifugation. After the supernatant was removed, the solid was dissolved in water again. The low molecular weight substances were removed with an ultrafiltration membrane (50K), and the filtrate was passed through a 0.22 µm filter, and lyophilized to obtain 280 mg of the target compound.

A solution of the aforementioned DDS compound prepared as 2.63 mg/ml in distilled water (10 µl) was added with 490 µl of a solution of α-chymotrypsin prepared as 2 mg/ml in Britton Robinson buffer (pH 6), or a solution of subtilisin A prepared as 2 mg/ml in Tris-HCl (pH 9). The reaction mixture was incubated at 40° C. for 2 hours, and added with 500 µl of 0.5 N HCl solution containing 50% of acetonitrile. The released hydrolysate [NH$_2$—(CH$_2$)$_4$—CO-DX-8951] was quantitatively measured by HPLC. For the HPLC analysis, a Symmetry C18 (4.6×100 mm; 3.5 µm, Watars Co.) column was used, and elution was performed with 0.1% trifluoroacetic acid solution containing 32% of organic solvent (methanol:acetonitrile=1:2), and the hydrolysate was detected by fluorescent spectroscopy (Ex. 375 nm and Em. 445 nm). As a result, the NH$_2$—(CH$_2$)$_4$—CO-DX-8951 was eluted at about 4.8 minutes. When the DX-8951 content in the above DDS compound was calculated to be 3.2% by using a calibration curve prepared with NH$_2$—(CH$_2$)$_4$—CO-DX-8951. On the other hand, when the DX-8951 content was calculated based on UV absorption of the aforementioned DDS compound by using a calibration curve prepared with DX-8951, the content was calculated as 2.9%.

Example 3

The DX-8951 content in the DDS compound prepared in Example 1 (Compound 1) was measured by using (1) subtilisin A (0.1 M Tris-HCl, pH 9.0), (2) α-chymotrypsin (0.1 M Tris-HCl, pH 8.0), and (3) thermolysin (0.1 M Tris-HCl/1 mM CaCl$_2$, pH 9.0). 10 µl of a solution of Compound 1 prepared as 400 µg/ml was added to 180 µl of a buffer for each enzyme (final concentration; 20 µg/ml). To this mixture, 10 µl of each enzyme prepared as 100 mg/ml in each buffer was added (final concentration; 5 mg/ml), and the mixture was allowed to react for 3 hours at 40° C. After the reaction, 200 µl of 0.5 N HCl solution containing 50% of acetonitrile was added to the mixture, and 10 µl of the mixture was analyzed by HPLC. For the HPLC analysis, a Symmetry C18 (4.6×250 mm) column was used, and elution was performed with 0.1 M AcONa buffer (pH 5.0) containing 31% of organic solvent (acetonitrile:methanoly=2:1). The hydrolysate was measured by fluorescent spectroscopy (Ex. 375 nm and Em. 445 nm), and the hydrolysate in the enzymatic reaction mixture was quantitatively determined by using calibration curves which were prepared by using solutions containing 2 nmol/ml of each of G-DX-8951, DX-8951 and DX-8951 bound with phenylalanine-glycine derived from the spacer of Compound 1 (FG-DX-8951). As a result, it was found that the subtilisin A and the α-chymotrypsin released 100% of G-DX-8951 from Compound 1 under the aforementioned conditions. The thermolysin released 100% of FG-DX-8951.

Example 4

Meth A cells subcultured in abdominal cavities were intraperitoneally transplanted into BALB/c (♂) mice (1×10$^6$ cells/mouse). After 5 days, Compound 1 (DX-8951 content: 5.2%) was intraperitoneally administered to the mice in an amount of 10 or 2.5 mg/kg (amount in terms of DX-8951). At 2, 4, 8, 24, and 48 hours after the administration, blood was collected from hearts. The collected blood was left for 10 minutes, and centrifuged at 12,000 rpm for 10 minutes to obtain blood serum. At the same time, tumorous ascites was also collected. 25 µl of the serum and the tumorous ascites were each added with 100 µl of water containing 80% of methanol, and centrifuged at 12,000 rpm for 5 minutes. 25 µl of the supernatant was added with 225 µl of a thermolysin solution prepared as 2 mg/ml in 0.1 M Tris-HCl, pH 8.5/0.1 M CaCl$_2$, and the mixture was allowed to react at 50° C. for 1 hour. Then, the reaction mixture was added with 250 µl of 0.5 N HCl solution containing 50% of acetonitrile, and 20 µl of the mixture was subjected to HPLC analysis. For the HPLC analysis, a Symmetry C18 (4.6×100 mm) column was used, and elution was performed with 0.1 M AcONa solution (pH 5.0) containing 41% of a mixture of methanol and acetonitrile (1:2), and the hydrolysate was detected by fluorescent spectroscopy (Ex. 375 nm and Em. 445 nm). As a result, when 10 mg/kg was administered, the concentration of Compound 1 in the ascites decreased with time, whilst the blood concentration gradually increased after the administration and reached the maximum concentration at 24 hours, and after then the concentration was kept at almost the same level as the ascites concentration (FIG. 1). When 2.5 mg/kg was administered, the changes in concentrations in blood and ascites were similar to those observed at 10 mg/kg administration.

Example 5

Figure 2:
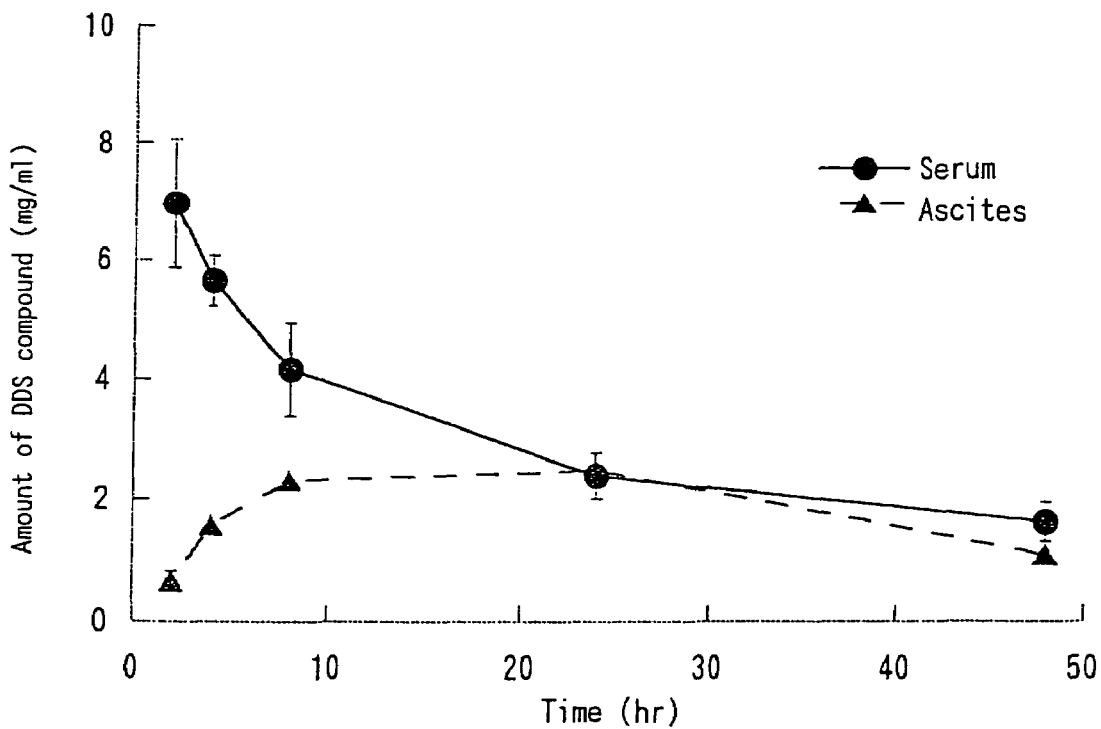
FIG. 2 shows blood and ascites concentrations of DDS compound measured by the method of the present invention (Example 5).

Meth A cells subcultured in abdominal cavities were intraperitoneally transplanted into BALB/c (♂) mice (1×10⁶ cells/mouse). After 5 days, Compound 1 (DX-8951 content: 6.6%) was intraperitoneally administered to the mice in an amount of 10 or 2.5 mg/kg (amount based on DX-8951, each group consisted of 3 mice). After the administration, blood was collected from hearts with time (5 and 30 minutes, and 2, 4, 8, 24, and 48 hours). The collected blood was left for 10 minutes, and centrifuged at 12,000 rpm for 10 minutes to obtain blood serum. At the same time, tumorous ascites was also collected. 25 μl of the serum and the tumorous ascites were each added with 225 μl of an α-chymotrypsin solution prepared as 2 mg/ml in Britton Robinson Buffer (pH 6), and the mixture was allowed to react at 40° C. for 2 hour. Then, the reaction mixture was added with 250 μl of 0.5 N HCl solution containing 50% of acetonitrile, and centrifuged at 12,000 rpm for 5 minutes, and 10 μl of the supernatant was subjected to HPLC analysis. Estimated concentrations of Compound 1 were calculated from the concentration of G-DX-8951 obtained by the HPLC analysis and the DX-8951 content of Compound 1 used. The HPLC analysis was performed under the same conditions as Example 4. As a result, when 10 mg/kg was administered, the concentration of Compound 1 in blood decreased with time. The concentration in ascites gradually increased after the administration, and reached substantially the same level as the blood concentration at 48 hours (FIG. 2). When 2.5 mg/kg was administered, the changes in concentrations of Compound 1 in blood and ascites were similar to those observed at 10 mg/kg administration.

Example 6

A DDS compound comprising a polymer carrier modified with a saccharide compound was prepared as follows. In the following scheme, only one or two constitutional units introduced with carboxymethyl groups were exemplified as the constitutional units of the saccharide chain, however, it should be understood that the carboxymethyldextran polyalcohol moiety of the DDS compounds described in the examples are not formed by the repetition of the constitutional units. The carboxymethylation degree (degree of substitution with carboxymethyl groups per saccharide residue as a building unit) was determined by converting the sodium salt of the carboxymethyldextran polyalcohol into free acid form, and then dissolving the free acid in aqueous 0.1 N sodium hydroxide and titrating the solution with 0.1 N hydrochloric acid. An aqueous solution of the sodium salt of the carboxymethyl-dextran polyalcohol was applied to a Bio-Rad AG50W-x2 (H⁺) column, and the passed solution was lyophilized and used as a sample. The sample was dissolved in a given excess amount of 0.1 N aqueous sodium hydroxide, and titrated with 0.1 N hydrochloric acid by using phenolphthalein as an indicator. The carboxymethylation degree was determined in accordance with the equation: $13.4(a-b)/[s-5.8(a-b)]$ wherein symbol "s" represents the amount of the collected sample (mg), symbol "a" represents the given excess amount of 0.1 N aqueous sodium hydroxide (ml), and symbol "b" represents the amount of 0.1 N hydrochloric acid required for the titration (ml). The amount of the introduced drug (% by weight) was calculated from the results of absorption spectrometry (around 362 nm) utilizing the characteristic absorption of the drug. The gel filtration was performed under the following conditions: column; TSK gel G4000 PW$_{XL}$, eluate; 0.1 M NaCl, flow rate; 0.8 ml/min, and column temperature; 40° C.

(A) Synthesis of Compound 2-2

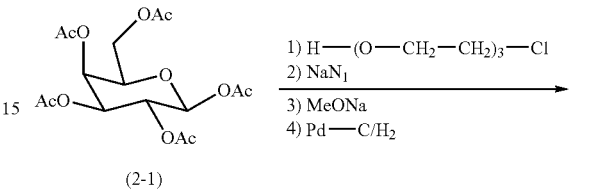

(2-1)

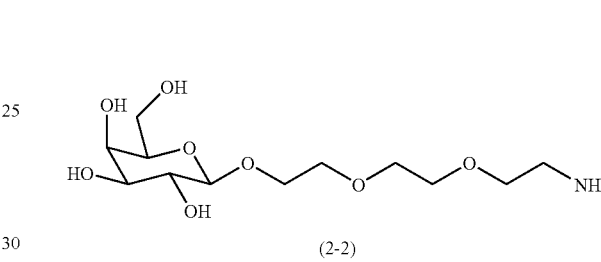

(2-2)

Compound 2-1 (5.0 g) and 2-[2-(2-chloroethoxy)ethoxy] ethanol (3.75 ml) were dissolved in dichloromethane (75 ml), and the solution was added with boron trifluoride ether complex (7.7 g) and stirred for 5 hours. The reaction mixture was diluted with dichloromethane (100 ml), and the organic layer was washed with water, saturated aqueous sodium hydrogencarbonate, and then with brine, and dried over magnesium sulfate. After the magnesium sulfate was removed by filtration, the solvent was evaporated, and the resulting residue was purified by column chromatography (hexane:ethyl acetate=2:1) using silica gel to obtain 3.3 g of chlorinated compound. The chlorinated compound obtained (3.3 g) and NaN₃ (2.0 g) were stirred at 60° C. for 2 days in DMF (15 ml). The solvent was evaporated, and the residue was dissolved in a mixture of ethyl acetate and water. The organic layer was washed with water, and dried over magnesium sulfate, and then the magnesium sulfate was removed by filtration. The solvent was evaporated to obtain 2.8 g of azide compound.

The azide compound obtained (1.5 g) was dissolved in methanol (30 ml), and the solution was added with a 28% MeONa solution in methanol until the pH reached 10, and the resulting mixture was stirred for 1 hour. Then, the reaction mixture was added with Dowex 50 WX8 (H⁺) until the mixture became neutral, and the resin was removed by filtration and the solvent was evaporated. The resulting residue was dissolved in a mixture of methanol (50 ml) and water (10 ml), and the solution was added with 5% Pd—C (water content; 50%, 2.0 g) and stirred overnight under hydrogen at ordinary pressure. The catalyst was removed by filtration, and the solvent was evaporated to obtain 1.2 g of Compound 2-2.

¹H-NMR (DMSO-d₆): δ 4.20–4.30 (1H, br), 4.00–4.10 (1H, br), 3.80–3.85 (1H, br), 3.50–3.75 (14H, m), 2.75–2.90 (2H, m)

(B) Synthesis of Galactose-modified CM-dextran Polyalcohol

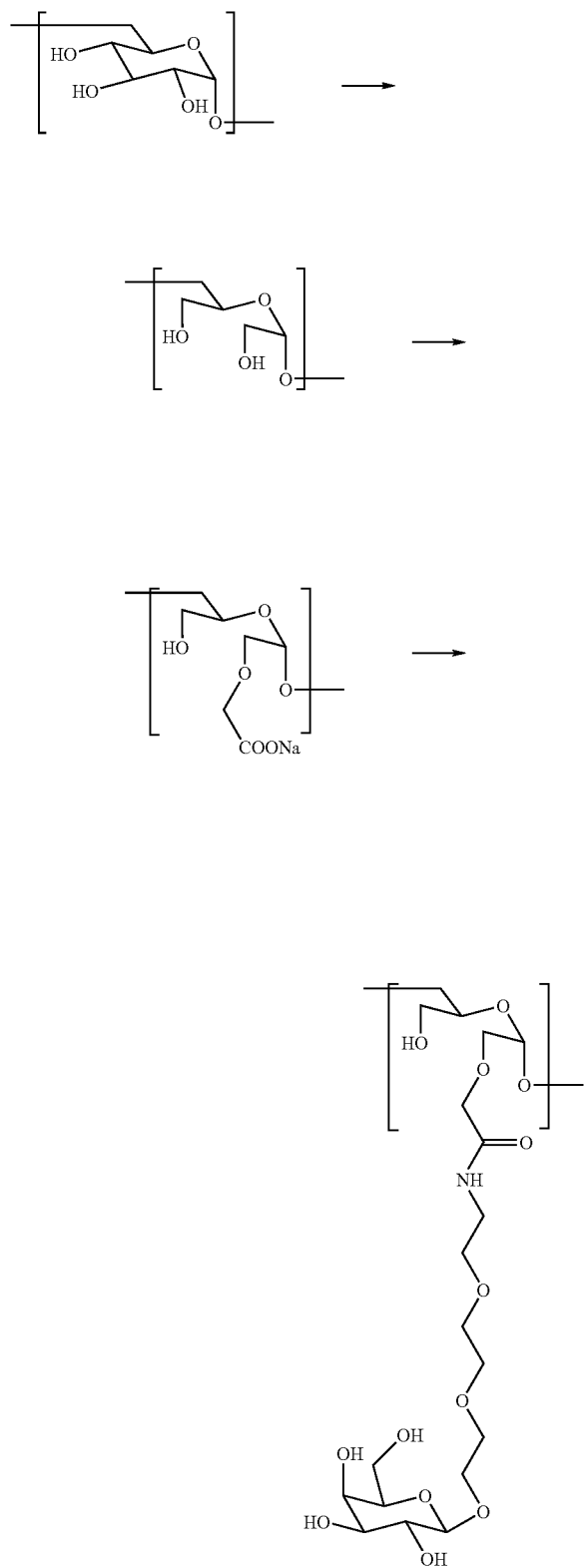

An aqueous solution (2000 ml) of sodium periodate (66.0 g) was added to 0.1 M solution of dextran 4 (Funakoshi Co. Ltd., average molecular weight; 4000–6000, 20 g) in acetate buffer (pH 5.5, 2000 ml). The mixture was shielded from the light and stirred at 4° C. for 10 days. Then, the mixture was added with ethylene glycol (14.0 ml) and stirred overnight. The reaction mixture was adjusted to pH 7.5 with 8 M aqueous sodium hydroxide under ice cooling, and added with sodium borohydride (28 g). After the sodium borohydride was dissolved, the mixture was stirred overnight at room temperature. The mixture was adjusted to pH 5.5 with acetic acid under ice cooling, and stirred at 4° C. for 1 hour. The mixture was adjusted to pH 7.5 with 8 M aqueous sodium hydroxide under ice cooling. The above procedure was repeated twice, and the resulting two butches of aqueous solution were combined, and low molecular weight fractions were removed by ultrafiltration using a Biomax-3 membrane (Millipore) to obtain a residual solution. The residual solution was passed through a Biomax-30 membrane. The passed solution was desalted by ultrafiltration using a Biomax-3 membrane and lyophilized to obtain purified dextran polyalcohol (12.0 g). The molecular weight (gel filtration, pullulan standard) of the resulting product was 9K.

The above purified dextran polyalcohol (9.4 g) was added to an aqueous solution obtained by dissolving-sodium hydroxide (39.3 g) in water (282 ml), and dissolved at room temperature. Monochloroacetic acid (56.4 g) was added to the solution under ice cooling and dissolved, and the mixture was allowed to react for 20 hours at room temperature. The reaction mixture was adjusted to pH 8 with acetic acid, and subjected to ultrafiltration using a Biomax-5 membrane to remove low molecular weight fractions. The residual solution was lyophilized to obtain sodium salt of carboxymethyl (abbreviated as "CM" hereinafter in the examples)-dextran-polyalcohol (12 g). The resulting sodium salt of CM-dextran polyalcohol (4.0 g) was added to an aqueous solution obtained by dissolving sodium hydroxide (17 g) in water (120 ml), and dissolved at room temperature. Monochloroacetic acid (24 g) was added to the solution under ice cooling and dissolved, and then the mixture was allowed to react for 20 hours at room temperature.

The reaction mixture was adjusted to pH 8 with acetic acid, and low molecular weight fractions were removed by ultrafiltration using a Biomax-5 membrane. The residual solution was lyophilized to obtain sodium salt of CM-dextran polyalcohol (4.0 g). The molecular weight (gel filtration, pullulan standard) of the resulting product was 14K, and the carboxymethylation degree per saccharide residue was 0.7 as determined by alkalimetry. The resulting sodium salt of CM-dextran polyalcohol (1.0 g) was dissolved in water (100 ml), and the solution was added with a methanol solution (100 ml) of Compound 2-2 (800 mg) of Example 1. The solution was further added with water-soluble carbodiimide hydrochloride (240 mg) 3 times every 2 hours, and then the mixture was stirred for 6 hours in total. The solvent in the reaction mixture was evaporated, and the resulting oil was dissolved in water and desalted by ultrafiltration using a Biomax-3 membrane. The resulting aqueous solution was lyophilized to obtain 1.1 g of the title compound. The galactose content in the product was 1.0 per 10 saccharide residues as determined by the phenol-sulfuric acid method.-

(C) Synthesis of Galactose-modified CM-dextran Polyalcohol-Gly-Gly-Phe-Gly-DX-8951 (SEQ ID NO. 1)

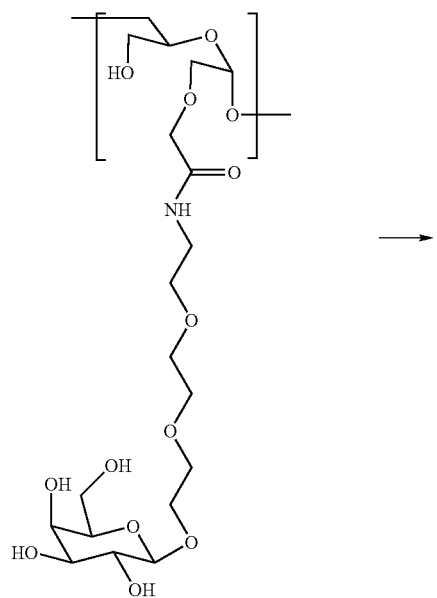

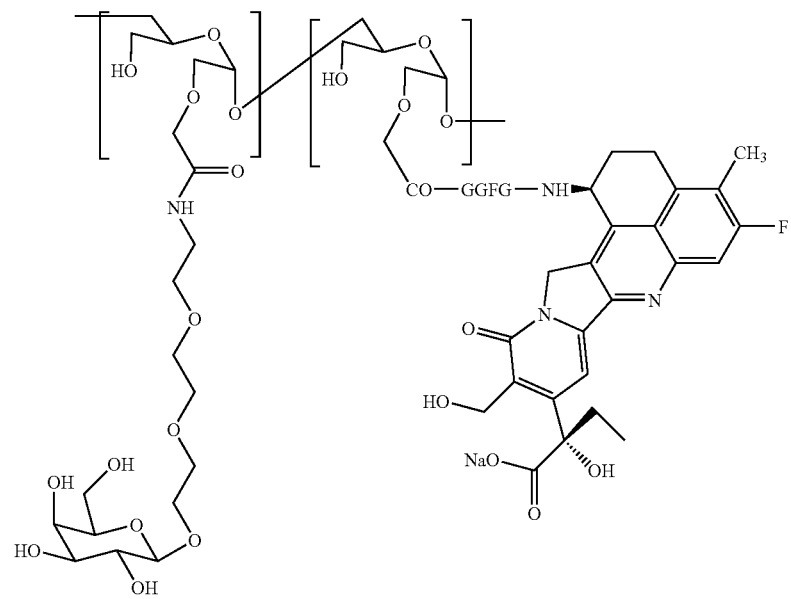

Figure 3:
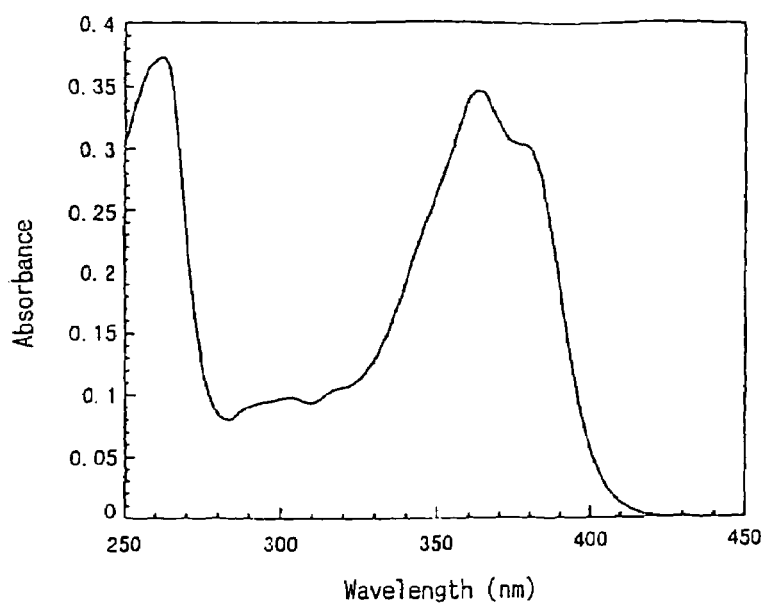
FIG. 3 shows an ultraviolet absorption spectrum of the DDS compound containing a polymer carrier modified with a saccharide compound (Example 6).
Figure 4:
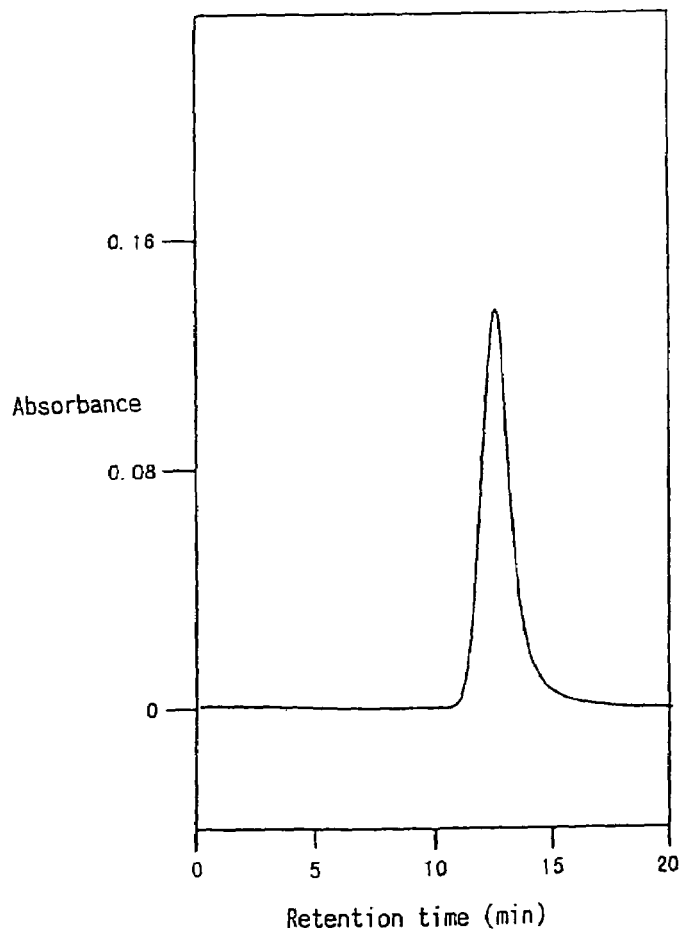
FIG. 4 shows a GPC chart of the DDS compound containing a polymer carrier modified with a saccharide compound (Example 6).

The sodium salt (1.0 g) of the galactose-modified CM-dextran polyalcohol obtained in the above (B) was dissolved in water (30 ml), and the solution was added with a solution of trifluoroacetic acid salt of Gly-Gly-Phe-Gly-DX-8951 (SEQ ID NO. 1) (150 mg) and 1-hydroxybenzotriazole (35 mg) in methanol (40 ml). The solution was adjusted to pH 7.0, and then added with water-soluble carbodiimide hydrochloride (35 mg) 3 times every 2 hours and stirred overnight. The solvent in the reaction mixture was removed by evaporation, and the resulting residue was dissolved in 3 M aqueous sodium chloride (20 ml), and the solution was added dropwise to ethanol (100 ml). The deposited precipitates were collected by centrifugation (3500 rpm, 8 minutes). The precipitates were dissolved in water and desalted by ultrafiltration using a Biomax-3 membrane. The residual solution, which did not pass through the membrane, was filtered through a Millipore filter (0.22 μm), and lyophilized to obtain 900 mg of the title compound. The resulting product was dissolved in 0.1 M aqueous sodium chloride, and analyzed by GPC (Column; TOSOH TSK GelPW-4000XL, solvent; 0.1 M aqueous NaCl, flow rate; 0.8 ml/min). The results of the GPC analysis and an ultraviolet absorption spectrum (in 0.1 M Tris buffer, pH 9.0) of the compound are shown in FIG. 3, respectively. The DX-8951 content in the compound was found as 4.9% (w/w) by quantitative analysis based on absorption spectrophotometry at 366 nm in 0.1 M Tris buffer containing 30% of acetonitrile (pH 10.0).

(D) Synthesis of CM-dextran Polyalcohol-Gly-Gly-Phe-Gly-DX-8951 (SEQ ID NO. 1)

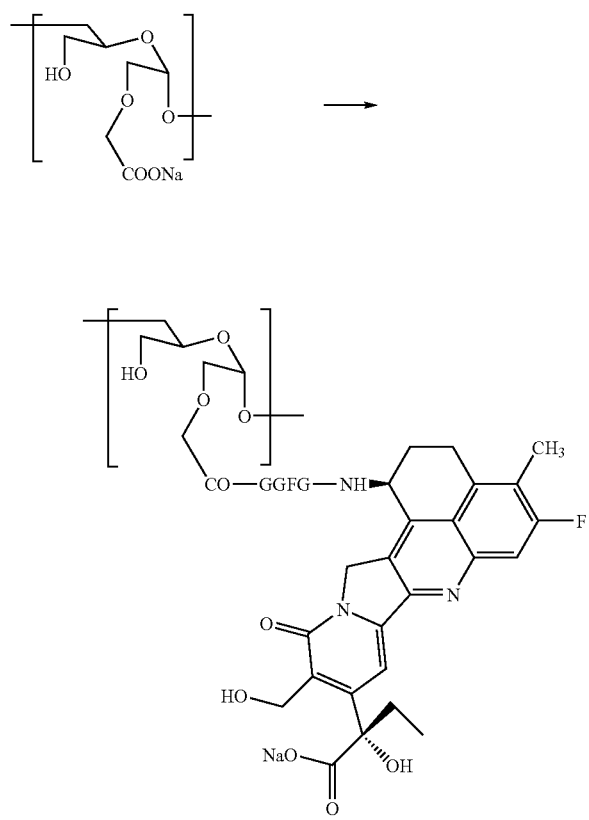

Figure 6:
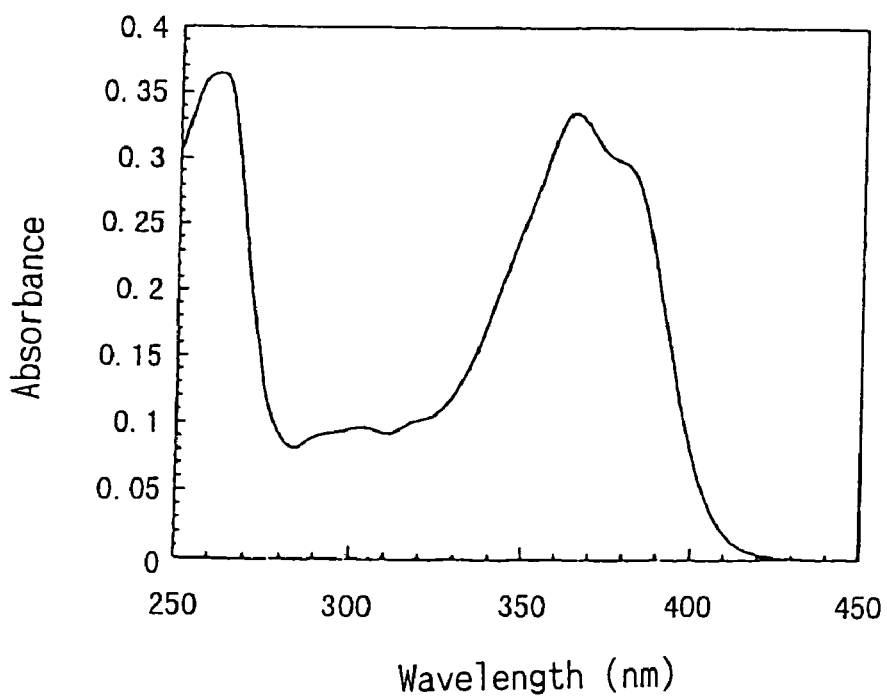
FIG. 6 shows an ultraviolet absorption spectrum of the DDS compound of the present invention (Example 6, (D)).

The sodium salt of the CM-dextran polyalcohol obtained in the above (B) (2.0 g) was dissolved in water, and the solution was passed through Dowex-50 WX8 (Et$_3$NH$^+$) to obtain triethylammonium salt of CM-dextran polyalcohol (1.9 g). The resulting triethylammonium salt of CM-dextran polyalcohol (1.9 g) was dissolved in an aqueous solution containing 50% of N,N-dimethylformamide. The solution was successively added with a solution of triethylamine (0.112 ml) and trifluoroacetic acid salt of Gly-Gly-Phe-Gly-DX-8951 (SEQ ID NO. 1) (350 mg) in N,N-dimethylformamide (10 ml), and 1-ethoxycarbonyl-2-ethoxy-1,2-dihydroxyquinoline (1.9 g), and the mixture was allowed to react overnight at room temperature with stirring. The solvent in the reaction mixture was removed by evaporation, and the resulting residue was dissolved in 3 M aqueous sodium chloride (20 ml), and the solution was added dropwise to ethanol (100 ml). The deposited precipitates were collected by centrifugation (3500 rpm). These precipitates were dissolved in water, and desalted by ultrafiltration using a Biomax-3 membrane. The residual solution that did not pass through the membrane was filtered by a Millipore filter (0.22 μm), and lyophilized to obtain 1.4 g of the title compound. The resulting product was dissolved in 0.1 M aqueous sodium chloride, and analyzed by GPC (Column; TOSOH TSK GelPW-4000XL, solvent; 0.1 M aqueous NaCl, flow rate; 0.8 ml/min). The result of the GPC analysis and ultraviolet absorption spectrum (in 0.1 M Tris buffer, pH 9.0) of the compound are shown in FIG. 6, respectively. The DX-8951 content in the compound was found as 5.2% (w/w) by quantitative analysis based on absorption spectrophotometry at 366 nm in 0.1 M Tris buffer containing 30% of acetonitrile (pH 10.0).

(E) Measurement of DDS Compound

The galactose-modified DDS compound obtained in the above (C), and the DDS compound of the above (D) as a control were each dissolved in distilled water for injection so as to give a concentration of 0.5 mg/ml based on DX-8951. Each of the aqueous solutions of the DDS compounds was intravenously injected to C57BL/6 mice (each group consisting of five mice) in the tails. The dose was 5 mg/kg based on DX-8951. After the administration, livers were extracted with time (0.5, 1, 2, 4, and 24 hours), and the amounts of the DDS compounds in the livers were determined. The liver was added with 5 times weight of water and homogenized. The homogenate was centrifuged at 3000 rpm for 10 minutes, and the supernatant was further centrifuged at 15,000 rpm for 15 minutes. 50 μl of the resulting supernatant was added with 450 μl of an α-chymotrypsin solution prepared as 2 mg/ml in Britton-Robinson Buffer (B.R.B), and the mixture was allowed to react at 40° C. for 2 hours. After then, the mixture was added with 500 μl of 0.5 N HCl solution containing 50% of acetonitrile, and centrifuged at 12,000 rpm for 5 minutes. The amount of released G-DX-8951 was measured by subjecting 20 μl of the supernatant to HPLC analysis to determine the amounts of DDS compounds. 50, 10, and 2 μg/ml aqueous solutions of each of the DDS compounds used for the administration were prepared in distilled water, and 50 μl of each solution was subjected to enzymatic treatment and G-DX8951 was quantified to prepare calibration curves.

Conditions of HPLC Analysis

Column: Symmetry C18 (4.6×100 mm)

Flow rate: 1.0 ml/min

Column temperature: 40° C.

Detection wavelength (fluorescence): Ex. 375 nm and Em. 445 nm

Eluate: methanol:acetonitrile=1:2 (29%), 0.1% TFA (71%)

Figure 5:
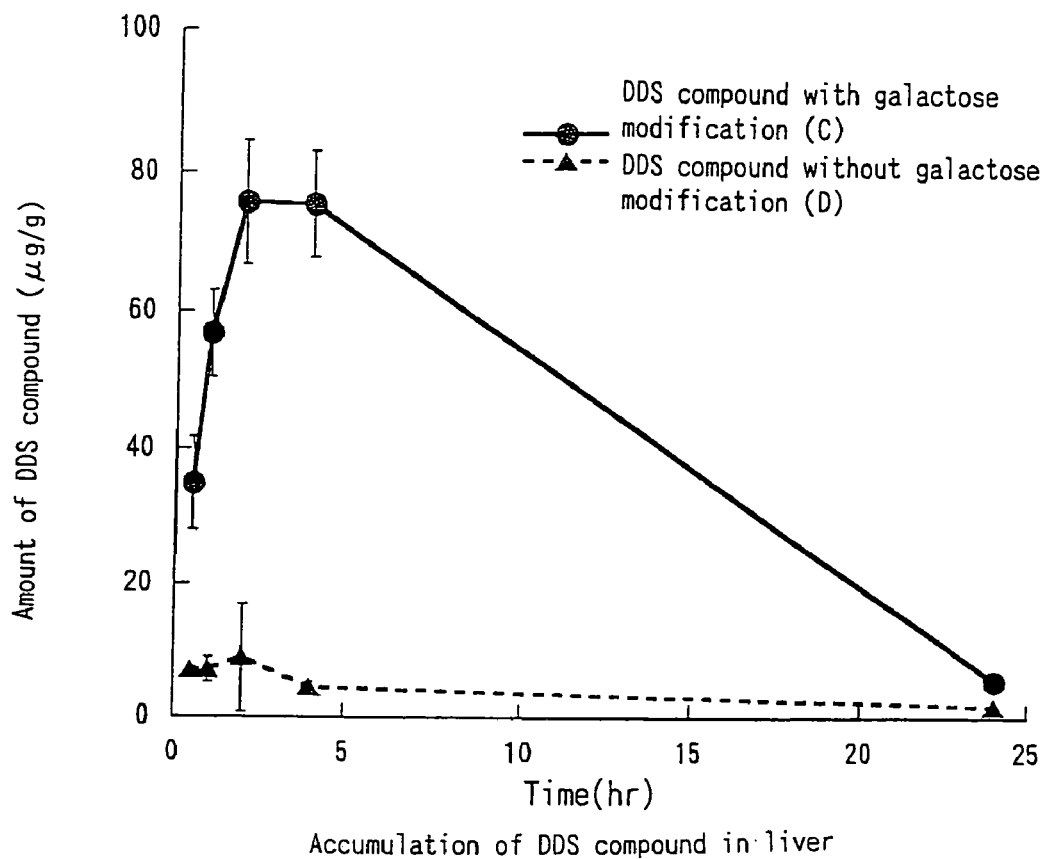
FIG. 5 shows the properties of the DDS compounds prepared in Example 6 ((C) and (D))which accumulated in liver.

The results are shown in FIG. 5. The aforementioned galactose-modified DDS compound exhibited higher liver accumulation compared to the control DDS compound (aforementioned (D)).

Example 7

Synthesis of Galactose-modified CM-dextran Polyalcohol-Gly-Gly-Phe-Gly-DX-8951

A solution of dextran T500 (Pharmacia, molecular weight; 500K, 50 g) in 0.1 M acetate buffer (pH 5.5, 5000 ml) was added with an aqueous solution (5000 ml) of sodium periodate (165.0 g). The solution was shielded from the light and stirred at 4° C. for ten days, and then added with ethylene glycol (35.0 ml) and stirred overnight. The reaction mixture was adjusted to pH 6.5 with 8 M aqueous sodium hydroxide under ice cooling, and added with a suspension of sodium borohydride (70 g) in water (2000 ml). After the sodium borohydride was dissolved, the solution was stirred overnight at room temperature. The solution was cooled on ice, adjusted to pH 5.5 with acetic acid, and stirred at 4° C. for one hour. The solution was adjusted to pH 7.5 with 8 M aqueous sodium hydroxide under ice cooling. The resulting solution was subjected to ultrafiltration using a Biomax-50 membrane to remove low molecular weight fractions and a residual solution was obtained. The residual solution was passed through an ultrafiltration membrane (1000K, Filtron Co.). The passed solution was desalted by ultrafiltration using a Biomax-50 membrane, and lyophilized to obtain dextran polyalcohol (21.1 g). The molecular weight (gel filtration, pullulan standard) of the product was 128K.

The resulting polyalcohol (5 g) was added to an aqueous solution obtained by dissolving sodium hydroxide (13.84 g) in water (150 ml), and dissolved in the solution at room temperature. Sodium salt of monochloroacetic acid (61.6 g) was added to the solution under ice cooling and dissolved in the solution, and then the mixture was allowed to react overnight at room temperature. The reaction mixture was adjusted to pH 8.5, and then low molecular weight fractions were removed by ultrafiltration using a Biomax-50 membrane. High molecular weight fractions were lyophilized to obtain sodium salt of CM-dextran polyalcohol (6.2 g). The molecular weight (gel filtration, pullulan standard) of the resulting product was 428K, and the degree of carboxymethylation per saccharide residue was found as 0.9 by alkalimetry. The resulting sodium salt of CM-dextran polyalcohol (500 mg) was dissolved in water (50 ml), and the solution was added with a solution of Compound 2-2 (400 mg) of Example 6 in methanol (20 ml) and a solution of 1-hydroxybenzotriazole (160 mg) in methanol (20 ml). The mixture was further added with water-soluble carbodiimide hydrochloride (120 mg) 3 times every 2 hours, and stirred for 6 hours in total. The solvent in the reaction mixture was removed by evaporation, and the resulting oil was dissolved in water and subjected to ultrafiltration using a Biomax-50 membrane to remove low molecular weight fractions. The residual solution was lyophilized to obtain 600 mg of the desired compound. The galactose content of the product was found as 1.7 per 10 saccharide residues determined by the phenol-sulfuric acid method.

Figure 7:
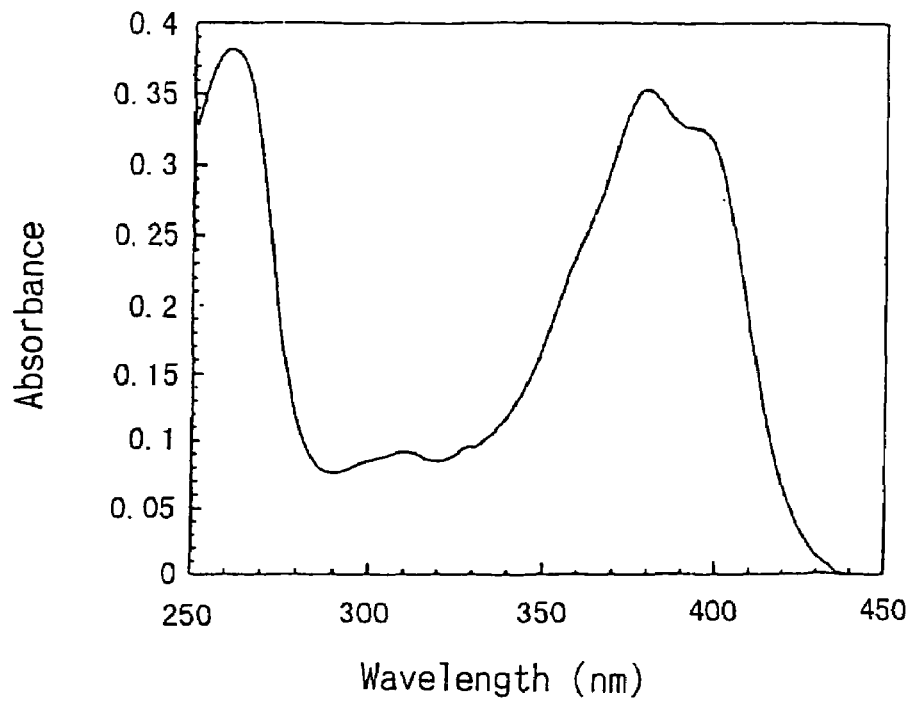
FIG. 7 shows an ultraviolet absorption spectrum of the DDS compound of the present invention (Example 7).
Figure 10:
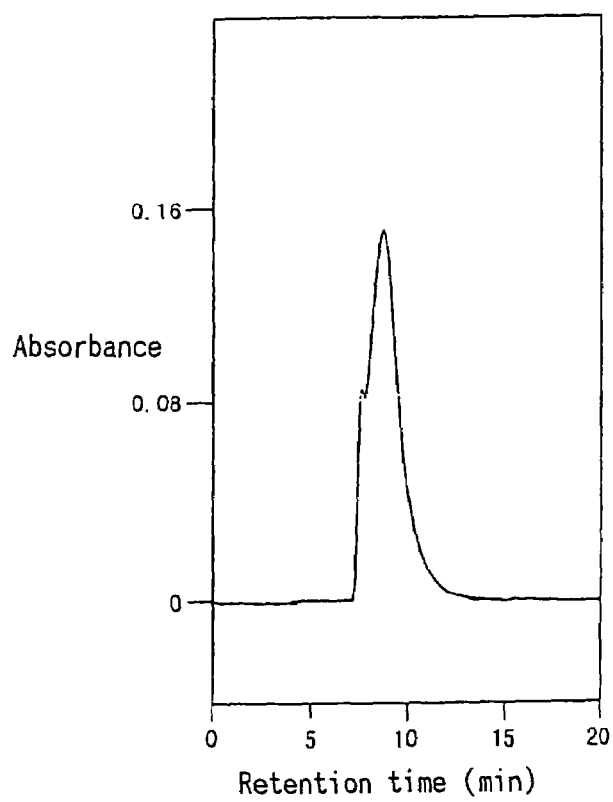
FIG. 10 shows a GPC chart of the DDS compound of the present invention (Example 7).

The resulting sodium salt of galactose-modified CM-dextran polyalcohol (200 mg) was dissolved in water (3 ml), and the solution was added with a solution of trifluoroacetic acid of Gly-Gly-Phe-Gly-DX-8951 (SEQ ID NO. 1) (27 mg) in methanol (3 ml) and a solution of 1-hydroxybenzotriazole (7 mg) in methanol (3 ml). The resulting solution was adjusted to pH 7.0, added with water-soluble carbodiimide hydrochloride (7 mg) 3 times every 2 hours, and stirred overnight. The solvent in the reaction mixture was removed by evaporation, and the resulting residue was dissolved in 3 M aqueous sodium chloride (10 ml), and then the solution was added dropwise to ethanol (100 ml). The deposited precipitates were collected by centrifugation (3500 rpm). The precipitates were dissolved in water, and desalted by ultrafiltration using a Biomax-50 membrane. The residual solution that did not pass through the membrane was filtered by a Millipore filter (0.22 µm), and lyophilized to obtain 180 mg of the title compound. The product was dissolved in 0.1 M aqueous sodium chloride, and analyzed by GPC (Column; TOSOH TSK GelPW-4000XL, solvent; 0.1 M NaCl aqueous solution, flow rate; 0.8 ml/min). The result of the GPC analysis and an ultraviolet absorption spectrum (in 0.1 M Tris buffer, pH 9.0) of the product are shown in FIGS. 10 and 7, respectively. The DX-8951 content in the product was and found as 3.7% (w/w) by quantitative analysis based on absorption spectrophotometry at 366 nm in 0.1 M Tris buffer containing 30% of acetonitrile (pH 10.0).

Example 8

Synthesis of 2-[2-(2-aminoethoxy)ethoxy]ethyl-β-D-2-amino-2-deoxygalactose

A solution of 2-[2-(2-azideethoxy)ethoxy]ethyl-β-D-2-acetylamino-2-deoxy- 3,4,6-triacetylgalactose (2.64 g) synthesized by the method described in Japanese Patent Unexamined Publication (KOKAI) (Hei) No.5-202085/1993 dissolved in methanol (10 ml) was cooled on ice. The solution was added with a 28% sodium methoxide solution in methanol (0.64 ml), and the mixture was stirred for 5 hours under ice cooling. The reaction mixture was added with acetic acid (0.186 ml), and dried under reduced pressure. The residue was purified by silica gel column chromatography (eluate; dichloromethane:methanol=9:1 solution) to obtain 2-[2-(2-azideethoxy)ethoxy]ethyl-β-D-2-amino-2-deoxygalactose (1.98 g).

$^1$H-NMR(CD$_3$OD) δ: 4.44 (d, 1H, J=8.8 Hz), 3.94–3.98 (m, 1H), 3.92 (dd, 1H, J=8.8, 10.7 Hz), 3.83 (d, 1H, J=2.9 Hz), 3.62–3.79 (m, 11H), 3.58 (dd, 1H, J=3.4, 10.7 Hz), 3.49 (dd, 1H, J=5.9, 6.3 Hz), 3.39 (t, 2H, J=4.9 Hz), 1.99 (s, 3H)

A solution of the aforementioned 2-[2-(2-azideethoxy)ethoxy]ethyl-β-D-2-amino-2-deoxygalactose (640 mg) dissolved in ethanol (10 ml) was added with the Lindlar catalyst (430 mg), the mixture was subjected to catalytic reduction for 1.5 hours under hydrogen at ordinary pressure. The Lindlar catalyst (215 mg) was further added to the mixture, and the catalytic reduction was performed for 3.5 hours under hydrogen at ordinary pressure. The catalyst was removed by filtration, and the filtrate was dried under reduced pressure to obtain 2-[2-(2-aminoethoxy)ethoxy]ethyl-β-D-2-amino-2-deoxygalactose (601 mg).

$^1$H-NMR(CD$_3$OD) δ: 4.32 (d, 1H, J=7.5 Hz), 3.80–3.91 (m, 2H), 3.30–3.75 (m, 14H), 2.73 (t, 2H, J=6.5 Hz), 1.98(s, 3H)

Example 9

Synthesis of N-acetylgalactosamine-modified CM-dextran Polyalcohol-Gly-Gly-Phe-Gly-DX-8951 (SEQ ID NO. 1)

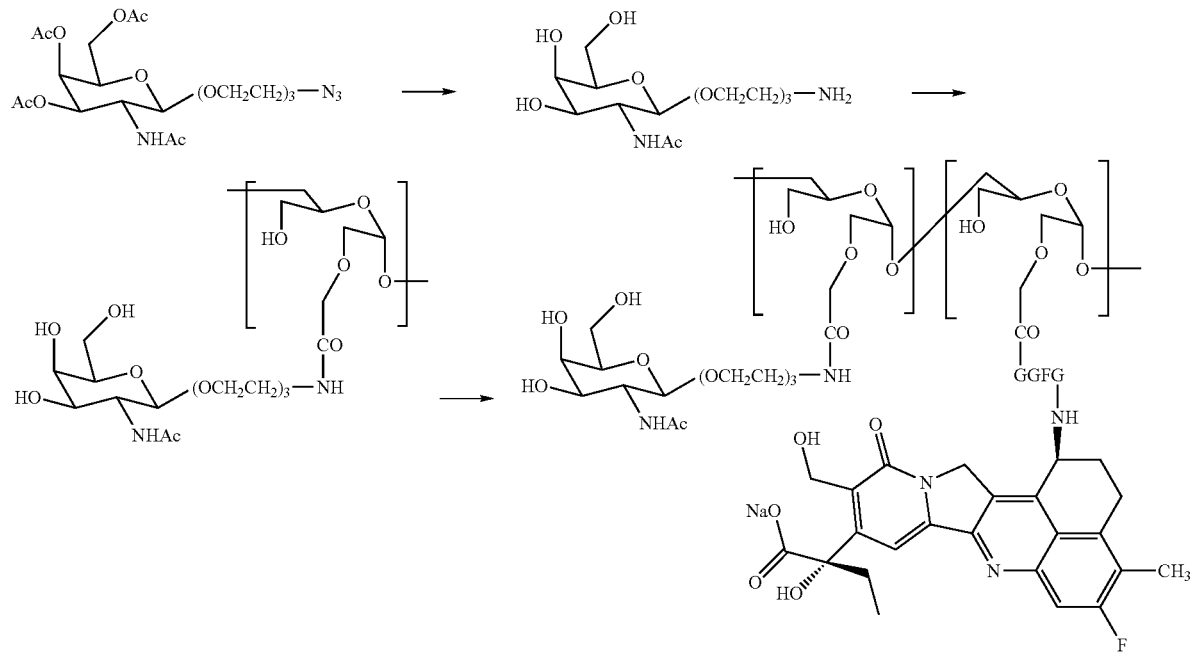

The sodium salt of CM-dextran polyalcohol obtained in Example 7 (375 mg) was dissolved in water (10 ml), and added with a solution of 2-[2-(2-aminoethoxy)-ethoxy]ethyl-β-D-2-amino-2-deoxygalactose (300 mg) obtained in Example 8 dissolved in methanol (10 ml) and a solution of 1-hydroxybenzotriazole (120 mg) dissolved in methanol (10 ml). The resulting solution was adjusted to pH 7.0, and added with water-soluble carbodiimide hydrochloride (90 mg) 3 times every 2 hours. The mixture was stirred overnight, and subjected to ultrafiltration using a Biomax-50 membrane to remove low molecular weight fractions from the reaction mixture. The residual solution that did not pass through the membrane was lyophilized to obtain N-acetylgalactosamine-modified CM-dextran polyalcohol (443 mg). The N-acetylgalactosamine content of the product was determined as 1.6 per 10 saccharide residues by the Elson-Morgan method.

Figure 8:
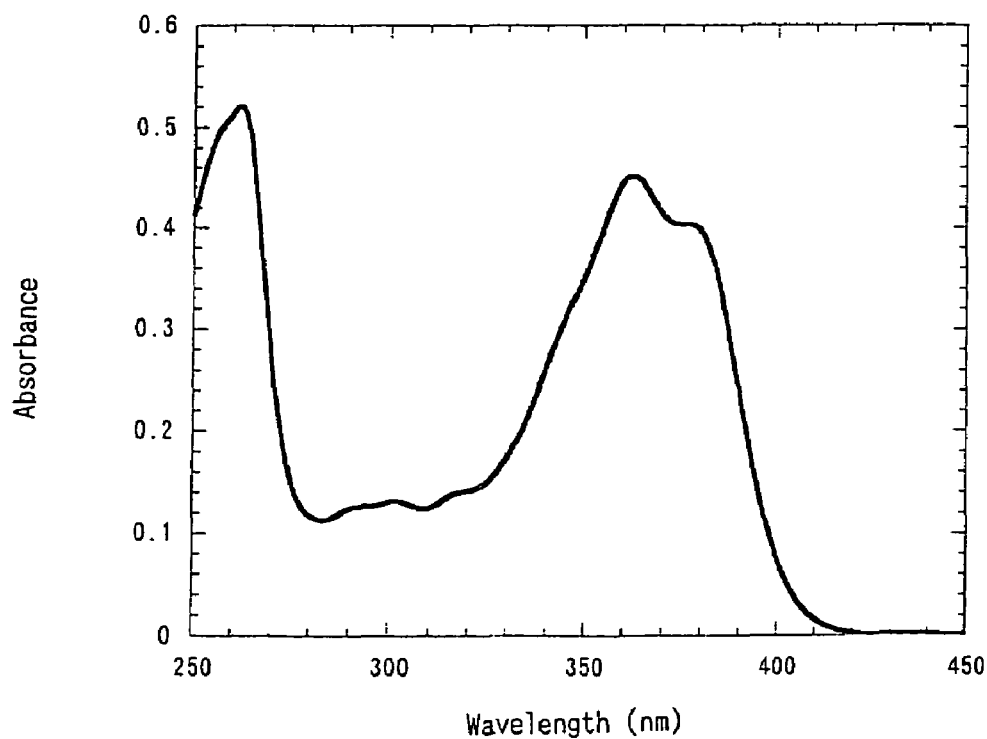
FIG. 8 shows an ultraviolet absorption spectrum of the DDS compound of the present invention (Example 9).
Figure 9:
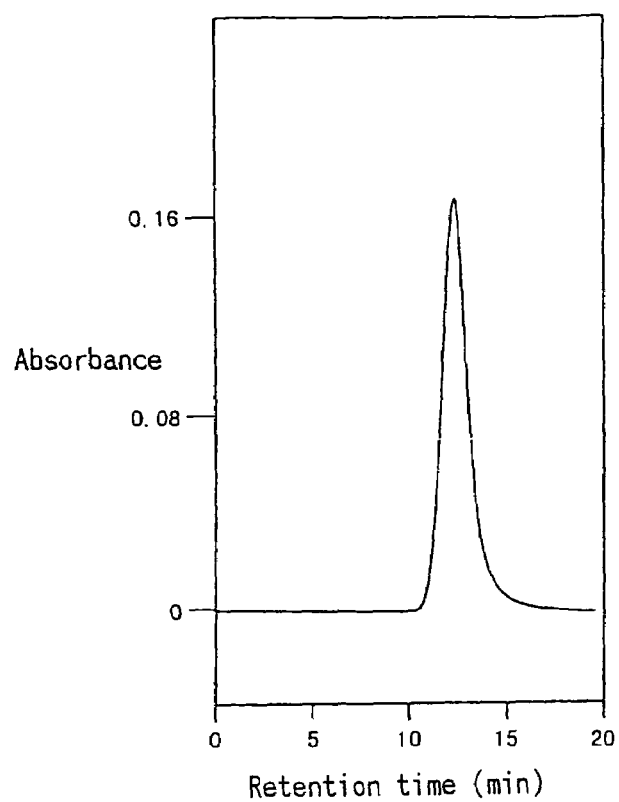
FIG. 9 shows a GPC chart of the DDS compound of the present invention (Example 6, (D)).
Figure 11:
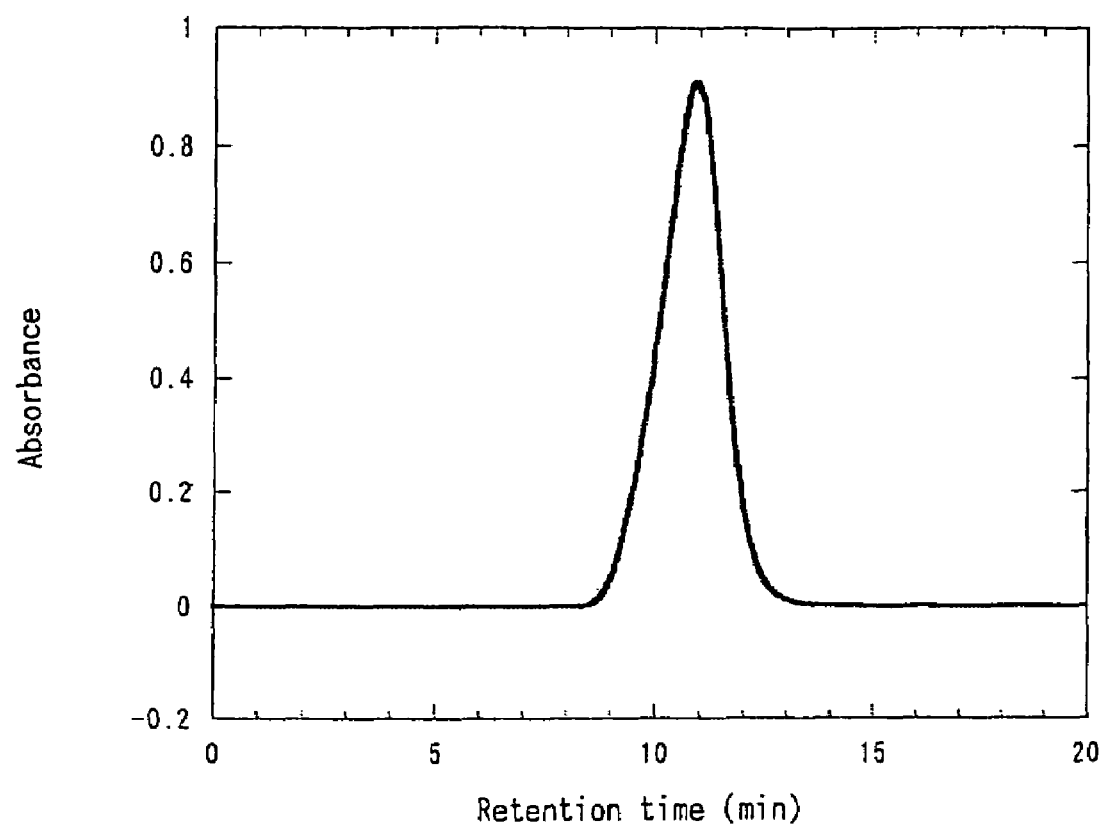
FIG. 11 shows a GPC chart of the DDS compound of the present invention (Example 9).

The resulting N-acetylgalactosamine-modified CM-dextran polyalcohol (200 mg) was dissolved in water (10 ml), and the solution was added with a solution of trifluoroacetic acid salt of Gly-Gly-Phe-Gly-DX-8951 (SEQ ID NO. 1) (30 mg) dissolved in methanol (10 ml), and a solution of 1-hydroxybenzotriazole (30 mg) dissolved in methanol (10 ml). The solution was adjusted to pH 7.0, and added with water-soluble carbodiimide hydrochloride (10 mg) 3 times every 2 hours. The mixture was stirred for 2 hours, and adjusted to pH 8.5. Low molecular weight fractions in the reaction mixture was removed by ultrafiltration using a Biomax -50 membrane. The residual solution that did not pass through the membrane was filtered through a Millipore filter (0.22 μm) and lyophilized to obtain the title compound (203 mg). The resulting product was dissolved in 0.1 M aqueous sodium chloride and then analyzed by GPC (Column; TOSOH TSK Gel PW-6000XL, solvent; 0.1 M acetate buffer (pH 5.0) containing 20% of acetonitrile, flow rate; 0.8 ml/min). The result of the GPC analysis and an ultraviolet absorption spectrum of this compound (0.1 M Tris buffer (pH 10.0):acetonitrile=7:3, 0.16 mg/ml) are shown in FIGS. 11 and 8, respectively. The content of drug compound residue in the product was found as 4.6% (w/w) by quantitative analysis based on absorption spectrophotometry at 366 nm in 0.1 M Tris buffer (pH 10.0):acetonitrile=7:3.

Example 10

Measurement of DX-8951 Content in CM-Dex-PA-Gly-Gly-Phe-Gly-NH—Y'—CH$_2$—O—CO-DX-8951 (SEQ ID NO. 1)

5 μl of a solution of CM-Dex-PA-Gly-Gly-Phe-Gly-NH—Y'—CH$_2$—O—CO-DX-8951 (SEQ ID NO. 1) (PABC means p-phenylene group) prepared as 1 mg/ml in distilled water was added with 95 μl of a papain solution prepared as 2 mg/ml in Britton Robinson buffer (pH 6). The reaction mixture was incubated at 40° C. for 4 hours, added with 100 μl of 0.5 N HCl solution containing 50% of acetonitrile, and content of the released hydrolysate [DX-8951] was determined by HPLC. For the HPLC analysis, a Symmetry C18 (4.6×100 mm; 3.5 μm, Watars Co.) column was used, and elution was performed with a 0.1% trifluoroacetic acid solution supplemented with an organic solvent (methanol:acetonitrile=1:2) so as to be a gradient from 20 to 70% for 12 minutes, and the hydrolysate was detected by fluorescent spectroscopy (Ex. 375 nm and Em. 445 nm). As the result, DX-8951 was eluted at about 5.7 minutes. The DX-8951 content in the above DDS compound was calculated as 4.0% by using a calibration curve prepared with DX-8951. On the other hand, the DX-8951 content was calculated as 3.3% based on UV absorption of the aforementioned DDS compound by using a calibration curve prepared with DX-8951.

Example 11

Measurement of DX-8951 Content in CM-Dex-PA-Gly-Gly-Gly-Phe-NH—Y'—CH$_2$—O—CO-DX-8951 (SEQ ID NO. 8)

5 µl of a solution of CM-Dex-PA-Gly-Gly-Gly-Phe-NH—Y'—CH$_2$—O—CO-DX-8951 (SEQ ID NO. 8) prepared as 1 mg/ml in distilled water was added with 95 µl of a solution of α-chymotrypsin prepared as 2 mg/ml in Britton Robinson buffer (pH 6). The reaction mixture was incubated at 40° C. for 4 hours and then added with 100 µl of 0.5 N HCl solution containing 50% of acetonitrile, and the content of the released hydrolysate [DX-8951] was determined by HPLC. For the HPLC alnalysis, a Symmetry C18 (4.6×100 mm; 3.5 µm, Watars Co.) column was used, and elution was performed with a 0.1% trifluoroacetic acid solution supplemented with an organic solvent (methanol:acetonitrile=1:2) so as to be a gradient from 20 to 70% for 12 minutes, and the hydrolysate was detected by fluorescent spectroscopy (Ex. 375 nm and Em. 445 nm). As a result, DX-8951 was eluted at about 5.7 minutes. The DX-8951 content in the above DDS compound was calculated as 2.5% by using a calibration curve prepared with DX-8951. On the other hand, the DX-8951 content was calculated as 1.7% based on UV absorption of the aforementioned DDS compound by using a calibration curve prepared with DX-8951.

Example 12

Measurement of DX-8951 Content in CM-Dex-PA-Gly-Gly-Phe-Gly-NH—(CH$_2$)$_4$—CO-DX-8951 (SEQ ID NO. 1)

5 µl of a solution of CM-Dex-PA-Gly-Gly-Phe-Gly-NH—(CH$_2$)$_4$—CO-DX-8951 (SEQ ID NO. 1) prepared as 100 µg/ml in distilled water was added with 95 µl of a papain solution prepared as 2 mg/ml in Britton Robinson buffer (pH 6). The reaction mixture was incubated at 40° C. for 4 hours and then added with 100 µl of 0.5 N HCl solution containing 50% of acetonitrile, and the content of the released hydrolysate [NH$_2$—(CH$_2$)$_4$—CO-DX-8951] was determined by HPLC. For the HPLC analysis, a Symmetry C18 (4.6×100 mm; 3.5 µm, Watars Co.) column was used, and elution was performed with 0.1% trifluoroacetic acid solution containing 32% of organic solvent (methanol:acetonitrile=1:2), and the hydrolysate was detected by fluorescent spectroscopy (Ex. 375 nm and Em. 445 nm). As a result, the NH$_2$—(CH$_2$)$_4$—CO-DX-8951 was eluted at about 5.3 minutes. The DX-8951 content in the above DDS compound was calculated as 3.0% by using a calibration curve prepared with NH$_2$—(CH$_2$)$_4$—CO-DX-8951. On the other hand, the DX-8951 content was calculated as 3.1% based on UV absorption of the aforementioned DDS compound by using a calibration curve prepared with DX-8951.

Example 13

Measurement of DXR Content in CM-Dex-PA-Gly-Gly-Phe-Gly-DXR (DXR: Doxorubicin) (SEQ ID NO. 1)

10 µl of a solution of the DDS compound prepared as 1 mg/ml in distilled water was added with 190 µl of a papain solution prepared as 2 mg/ml in Britton Robinson buffer (pH 6). The reaction mixture was incubated at 40° C. for 2 hours, and added with 200 µl of acetonitrile, and the content of the released hydrolysate [DXR] was determined by HPLC. For the HPLC analysis, a Symmetry C18 (4.6×100 mm; 3.5 µm, Watars Co.) column was used, elution was performed with 0.1% trifluoroacetic acid solution containing 34% of organic solvent (methanol:acetonitrile=1:2), and the hydrolysate was detected by fluorescent spectroscopy (Ex. 480 nm and Em. 590 nm). As a result, the DXR was eluted at about 3.8 minutes. The DXR content in the above DDS compound was calculated as 5.3% by using a calibration curve prepared with DXR. On the other hand, the DXR content was calculated as 4.3% based on UV absorption of the aforementioned DDS compound by using a calibration curve prepared with DXR.

Example 14

Synthesis of CM-dextran Polyalcohol-Gly-Gly-Phe-Gly-DXR (SEQ ID NO. 1)

Sodium salt of carboxymethyldextran polyalcohol (30 mg) having an average molecular weight of 274K and a carboxymethylation degree (degree of substitution with carboxymethyl groups per constitutional saccharide residue) of 0.4, which was prepared according to the method described in Example 24 of WO97/46260, was dissolved in 0.05 M collidine-HCl buffer (2 ml) containing 50% of methanol. The solution was added with a solution of hydrochloride of Gly-Gly-Phe-Gly-DXR (SEQ ID NO. 1) (4 mg) in methanol (400 µl), which hydrochloride was prepared according to the method described in Example 43 of WO97/46260, and a solution of 1-ethyl-3-(3-dimethyl-aminopropyl)carbodiimide hydrochloride (2.4 mg) in methanol (240 µl), and stirred for 2 hours. The solution was added with 30 ml of 3 M brine, and desalted by ultrafiltration using a Biomax-50K membrane. The residual solution that did not pass through the membrane was filtered by a Millipore filter (0.22 µm), and lyophilized to obtain the title compound (25 mg). The content of the drug compound residue in this compound was determined as 4.3% (w/w) by absorption spectrophotometry at 480 nm in PBS (pH 7.4).

Example 15

Synthesis of CM-Dex-PA-Gly-Gly-Phe-Gly-NH—(CH$_2$)$_4$—O-DX-8951 (SEQ ID NO. 1)

Boc-Gly-Gly-Phe-Gly-OH (SEQ ID NO. 1) (575 mg), HOSu (182 mg), and DCC (326 mg) were dissolved in DMF (20 ml), and the solution was stirred for 30 minutes. The resulting solution was added with a solution of p-toluenesulfonic acid salt of 5-aminopentanoic acid benzyl ester (500 mg) and triethylamine (0.184 ml) dissolved in DMF (10 ml), and the mixture was stirred at room temperature for three days. The reaction mixture was concentrated, and the residue was purified by column chromatography (CH$_2$Cl$_2$:MeOH=20:1) to obtain 560 mg of Boc-Gly-Gly-Phe-Gly-NH—(CH$_2$)$_4$—COOBzl (SEQ ID NO. 1). The Boc-Gly-Gly-Phe-Gly-NH—(CH$_2$)$_4$—COOBzl (SEQ ID NO. 1) (560 mg) was dissolved in methanol (60 ml) containing 50% of water, and the solution was added with 5% Pd—C (water content; 50%, 1.5 g) and stirred overnight under hydrogen at ordinary pressure. After the catalyst was removed from the reaction mixture by filtration, the mixture was concentrated to dryness to obtain 300 mg of Boc-Gly-Gly-Phe-Gly-NH—(CH$_2$)$_4$—COOH (SEQ ID NO. 1).

The Boc-Gly-Gly-Phe-Gly-NH—(CH$_2$)$_4$—COOH (SEQ ID NO. 1) (300 mg), DCC (138 mg) and HOSu (77 mg) were dissolved in DMF, and the solution was stirred for 30 minutes. The resulting solution was added with a solution of DX-8951 (317 mg) and triethylamine (0.078 ml) dissolved in DMF, and the mixture was stirred at room temperature overnight. The reaction mixture was concentrated, and the resulting residue was purified by column chromatography (CH$_2$Cl$_2$:MeOH=10:1) to obtain 400 mg of Boc-Gly-Gly-Phe-Gly-NH—(CH$_2$)$_4$—CO-DX-8951 (SEQ ID NO. 1).

The Boc-Gly-Gly-Phe-Gly-NH—(CH$_2$)$_4$—CO-DX-8951 (SEQ ID NO. 1) (300 mg) was dissolved in TFA (2 ml), and the solution was allowed to react for one hour, and then the reaction mixture was concentrated. The resulting residue was solidified by addition of ether, and the supernatant was removed. The solid mass was dried to obtain 250 mg of trifluoroacetic acid salt of H-Gly-Gly-Phe-Gly-NH—(CH$_2$)$_4$—CO-DX-8951 (SEQ ID NO. 1).

$^1$H-NMR(DMSO-d$_6$): δ 8.45–8.55 (m, 2H), 8.28–8.35 (m, 2H), 7.95–8.10 (br, 2H), 7.79 (d, 1H, J=10.7 Hz), 7.70–7.75 (m, 1H), 7.32 (s, 1H), 7.20–7.30 (m, 5H), 7.15–7.25 (m, 4H), 6.50–6.60 (br, 1H), 5.50–5.60 (m, 1H), 5.40–5.50 (m, 2H), 5.18 (s, 2H), 4.50–4.60 (m, 1H), 3.55–3.95 (m, 7H), 3.00–3.25 (m, 5H), 2.75–2.85 (m, 1H), 2.50 (s, 3H), 2.15–2.25 (m, 4H), 1.86–2.00 (m, 2H), 1.55–1.65 (m, 2H), 1.45–1.55 (m, 2H), 0.88 (t, 3H, J=7.35 Hz)

Triethylammonium salt of carboxymethyldextran polyalcohol (200 mg) having an average molecular weight of 337K and a carboxymethylation degree (degree of substitution with carboxymethyl groups per constitutional saccharide residue) of 0.4, which was prepared according to the method described in Example 24 of WO97/46260, was dissolved in DMF (10 ml). The above solution was added with a solution of trifluoroacetic acid salt of H-Gly-Gly-Phe-Gly-NH—(CH$_2$)$_4$—CO-DX-8951 (SEQ ID NO. 1) (30 mg) and triethylamine (10 μl) in methanol (4 ml), further added with a solution of 1-ethoxycarbonyl-2-ethoxy-1,2-dihydroxyquinoline (200 mg) in methanol (3 ml), and stirred overnight at room temperature with light shielding. The reaction mixture was diluted with 3 M brine, and low molecular weight fractions were removed by an ultrafiltration membrane (50K), and the resulting residue was passed through a 0.22 μm filter and lyophilized to obtain 178 mg of the target compound.

INDUSTRIAL AVAILABILITY

The DDS compound of the present invention, which utilizes a carboxy(C$_{1-4}$)-alkyldextran polyalcohol modified with a saccharide compound as a polymer carrier, has an extremely high organ selectivity, and is useful as a medicament that achieves excellent therapeutic effect. The method for measuring a DDS compound of the present invention can be utilized as an extremely useful method for clinical application of a DDS compound, because the method enables accurate and simple determination of blood concentration of the DDS compound or the content of a residue of a drug compound introduced to the DDS compound.

What is claimed is:

1. A drug delivery system compound which comprises a carboxy($C_{1-4}$)alkyl-dextran polyalcohol modified with galactose or galactosamine and a residue of drug compound bound to the carboxy($C_{1-4}$)alkyldextran polyalcohol.

2. The drug delivery system compound according to claim 1, wherein the carboxy($C_{1-4}$)alkyldextran polyalcohol modified with galactose or galactosamine and the residue of drug compound are bound to each other by a spacer.

3. The drug delivery system compound according to claim 2, wherein the spacer comprises one amino acid or 2 to 8 amino acids linked by peptide bond(s).

4. The drug delivery system compound according to claim 1, wherein the carboxy($C_{1-4}$) alkyldextran polyalcohol modified with galactose or galactosamine is formed by binding the galactose or galactosamine and a carboxy($C_{1-4}$) alkyldextran polyalcohol by a linker.

5. The drug delivery system compound according to claim 4, wherein the carboxy($C_{1-4}$)alkyldextran polyalcohol modified with galactose or galactosamine has a cluster modification by galactose or galactosamine bound by a linker.

6. A drug delivery system compound which is obtainable by binding a residue of a drug compound to a carboxy($C_{1-4}$)alkyldextran polyalcohol in which a part of carboxyl groups of the carboxy($C_{1-4}$)alkyl moiety are modified with galactose or galactosamine.

7. The drug delivery system compound according to claim 6, which is obtainable by binding the carboxy($C_{1-4}$)alkyldextran polyalcohol and the residue of drug compound by a spacer.

8. The drug delivery system compound according to claim 6, which is obtainable by binding the residue of drug compound to the carboxy($C_{1-4}$)alkyldextran polyalcohol which is produced by binding the galactose or galactosamine or a linker bound with the galactose or galactosamine to a part of carboxyl groups of the carboxy($C_{1-4}$)alkyl moiety of the carboxy($C_{1-4}$)alkyldextran polyalcohol.

9. A drug delivery system compound which is obtainable by modifying with galactose or galactosamine a carboxy ($C_{1-4}$)alkyldextran polyalcohol in which a residue of a drug compound is bound to a part of carboxyl groups of the carboxy($C_{1-4}$)alkyl moiety by a spacer.

10. The drug delivery system compound according to claim 9, which is obtainable by binding the carboxy($C_{1-4}$) alkyldextran polyalcohol and the galactose or galactosamine by a linker.

11. The drug delivery system compound according to claim 9, which is obtainable by modifying with galactose or galactosamine a carboxy($C_{1-4}$)alkyldextran polyalcohol produced by binding a residue of drug compound to a part of carboxyl groups of the carboxy ($C_{1-4}$)alkyl moiety of the carboxy($C_{1-4}$)alkyldextran polyalcohol by a spacer comprising one amino acid or a spacer comprising 2 to 8 amino acids linked by peptide bond(s).

12. The drug delivery system compound according to claim 1, wherein substitution degree of galactose or galactosamine, or clustered galactose or galactosamine is 0.01–1.0 per saccharide residue of the carboxy($C_{1-4}$)alkyldextran polyalcohol.

13. The drug delivery system compound according to claim 1, wherein the dextran polyalcohol that constitutes the carboxy($C_{1-4}$)alkyldextran polyalcohol is a dextran polyalcohol which is obtained by treating dextran under conditions that enable substantially complete polyalcoholization.

14. The drug delivery system compound according to claim 1, wherein the carboxy($C_{1-4}$)alkyldextran polyalcohol is carboxymethyldextran polyalcohol.

15. The drug delivery system compound according to claim 1, wherein the drug compound is an antineoplastic agent or an anti-inflammatory agent.

16. The drug delivery system compound according to claim 15, wherein the drug compound is an antineoplastic agent.

17. The drug delivery system compound according to claim 1, wherein the drug compound is (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13 (9H,15H)-dione.

18. The drug delivery system compound according to claim 17, which is a medicament for treating liver cancer.

19. A carboxy($C_{1-4}$)alkyldextran polyalcohol modified with galactose or galactosamine.

20. A polymer carrier comprising a carboxy($C_{1-4}$)alkyldextran polyalcohol modified with galactose or galactosamine.

* * * * *

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Spacer Sequence

<400> SEQUENCE: 1

Gly Gly Phe Gly
1

<210> SEQ ID NO 2
<211> LENGTH: 4
<212> TYPE: PRT
<213> ORGANISM: Artificial Sequence
<220> FEATURE:
<223> OTHER INFORMATION: Spacer Sequence

<400> SEQUENCE: 2

Gly Phe Gly Gly
1

<210> SEQ ID NO 3
<211> LENGTH: 4
<212> TYPE: PRT
<213> ORGANISM: Artificial Sequence
<220> FEATURE:
<223> OTHER INFORMATION: Spacer Sequence

<400> SEQUENCE: 3
```

Phe Gly Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: Spacer Sequence

<400> SEQUENCE: 4

Phe Phe Gly Gly
1

<210> SEQ ID NO 5
<211> LENGTH: 5
<212> TYPE: PRT
<213> ORGANISM: Artificial Sequence
<220> FEATURE:
<223> OTHER INFORMATION: Spacer Sequence

<400> SEQUENCE: 5

Gly Gly Gly Phe Gly
1               5

<210> SEQ ID NO 6
<211> LENGTH: 4
<212> TYPE: PRT
<213> ORGANISM: Artificial Sequence
<220> FEATURE:
<223> OTHER INFORMATION: Spacer Sequence

<400> SEQUENCE: 6

Gly Gly Phe Phe
1

<210> SEQ ID NO 7
<211> LENGTH: 6
<212> TYPE: PRT
<213> ORGANISM: Artificial Sequence
<220> FEATURE:
<223> OTHER INFORMATION: Spacer Sequence

<400> SEQUENCE: 7

Gly Gly Gly Gly Gly Gly
1               5

<210> SEQ ID NO 8
<211> LENGTH: 4
<212> TYPE: PRT
<213> ORGANISM: Artificial Sequence
<220> FEATURE:
<223> OTHER INFORMATION: Spacer Sequence

<400> SEQUENCE: 8

Gly Gly Gly Phe
1

<210> SEQ ID NO 9
<211> LENGTH: 4
<212> TYPE: PRT
<213> ORGANISM: Artificial Sequence

```
<220> FEATURE:
<223> OTHER INFORMATION: Spacer Sequence

<400> SEQUENCE: 9

Gly Gly Gly Gly
1
```